(12) United States Patent
Scholten et al.

(10) Patent No.: US 9,307,963 B2
(45) Date of Patent: Apr. 12, 2016

(54) GAS-OPERATED SURGICAL INSTRUMENT

(71) Applicant: Aesculap AG, Tuttlingen (DE)

(72) Inventors: Thomas Scholten, Tuttlingen (DE); Rupert Mayenberger, Rielasingen (DE)

(73) Assignee: Aesculap AG, Tuttlingen (DE)

( * ) Notice: Subject to any disclaimer, the term of this patent is extended or adjusted under 35 U.S.C. 154(b) by 522 days.

(21) Appl. No.: 13/693,086

(22) Filed: Dec. 4, 2012

(65) Prior Publication Data

US 2013/0150854 A1 Jun. 13, 2013

Related U.S. Application Data

(63) Continuation of application No. PCT/EP2011/059647, filed on Jun. 10, 2011.

(30) Foreign Application Priority Data

Jun. 16, 2010 (DE) .......................... 10 2010 017 395

(51) Int. Cl.
*A61B 17/00* (2006.01)
*A61B 17/16* (2006.01)

(52) U.S. Cl.
CPC .............. *A61B 17/00* (2013.01); *A61B 17/16* (2013.01); *A61B 17/1611* (2013.01); *A61B 2017/00544* (2013.01); *A61B 2017/00548* (2013.01)

(58) Field of Classification Search
CPC ........... A61B 17/1606; A61B 17/1608; A61B 17/1611; A61B 2017/00544; A61B 2017/00548

USPC ...................................................... 606/79–85
See application file for complete search history.

(56) References Cited

U.S. PATENT DOCUMENTS

| 4,349,028 | A | * | 9/1982 | Green | ............................ 606/143 |
| 8,038,677 | B2 | | 10/2011 | Schulz et al. | |
| 2007/0213769 | A1 | | 9/2007 | Schulz et al. | |
| 2010/0178100 | A1 | | 7/2010 | Fricke et al. | |
| 2011/0306979 | A1 | | 12/2011 | Schulz et al. | |

FOREIGN PATENT DOCUMENTS

| DE | 31 52 411 | 8/1986 |
| DE | 203 18 275 | 3/2004 |
| DE | 20 2009 009 737 | 2/2010 |
| WO | WO 2006/037542 | 4/2006 |
| WO | WO 2008/040537 | 4/2008 |

* cited by examiner

*Primary Examiner* — Si Ming Ku

(74) *Attorney, Agent, or Firm* — Lipsitz & McAllister, LLC

(57) ABSTRACT

A gas operated surgical instrument is provided. The instrument includes a pressurized gas connection for connection to a source of pressurized gas, a working piston adapted to be acted upon by a pressurized gas, an actuating element for actuating the instrument, and a regulating device coupled to the actuating element and to the working piston for regulating a feed force of the working piston. The regulating device is configured such that, for feed forces below a predetermined limit force, it defines a first work area in which the working piston is movable in the distal direction solely owing to a feed force applied with the actuating element, and that above the limit force the regulating device defines a second work area in which the working piston is movable in the distal direction by being acted upon by pressurized gas.

25 Claims, 15 Drawing Sheets

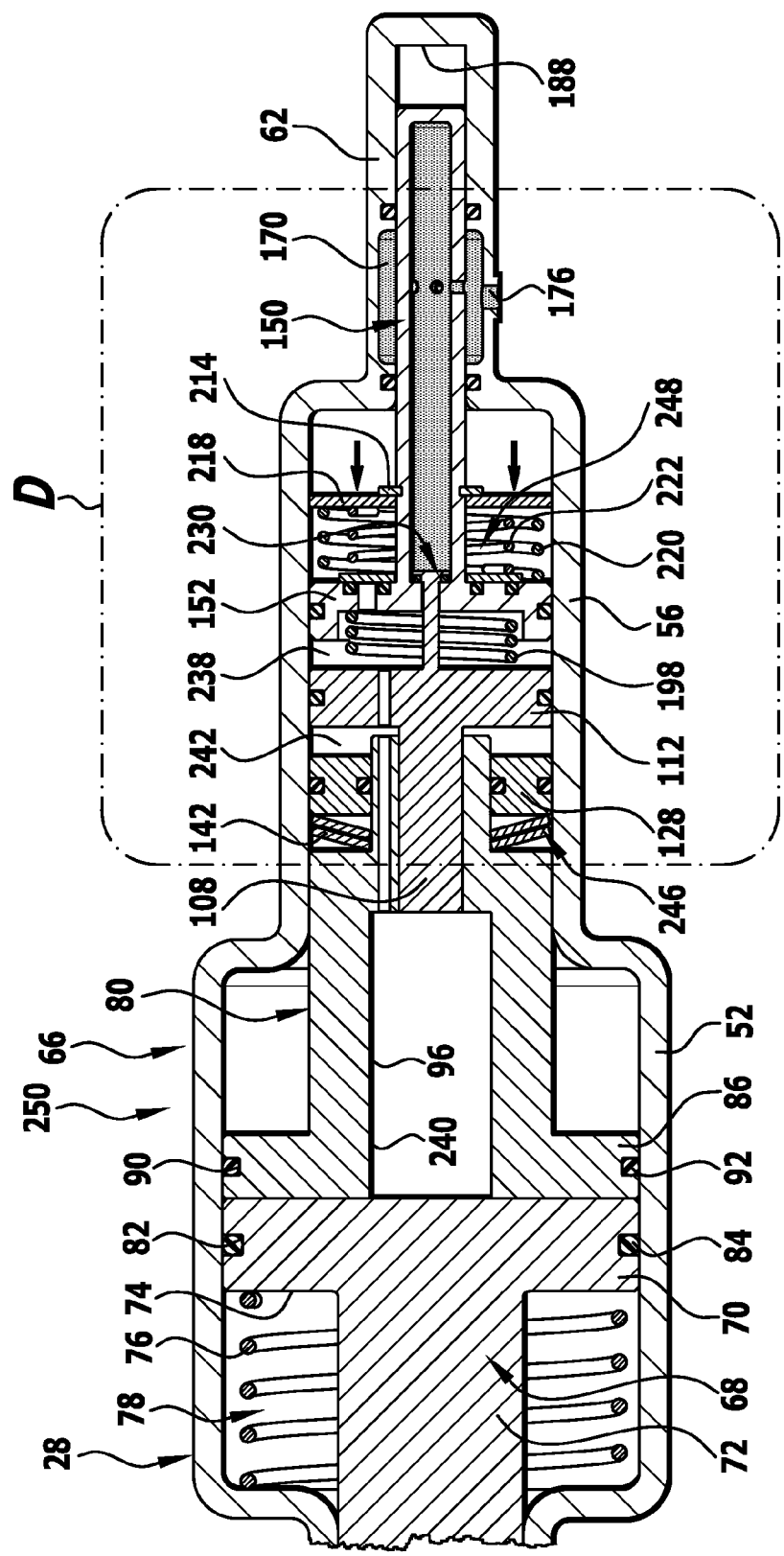

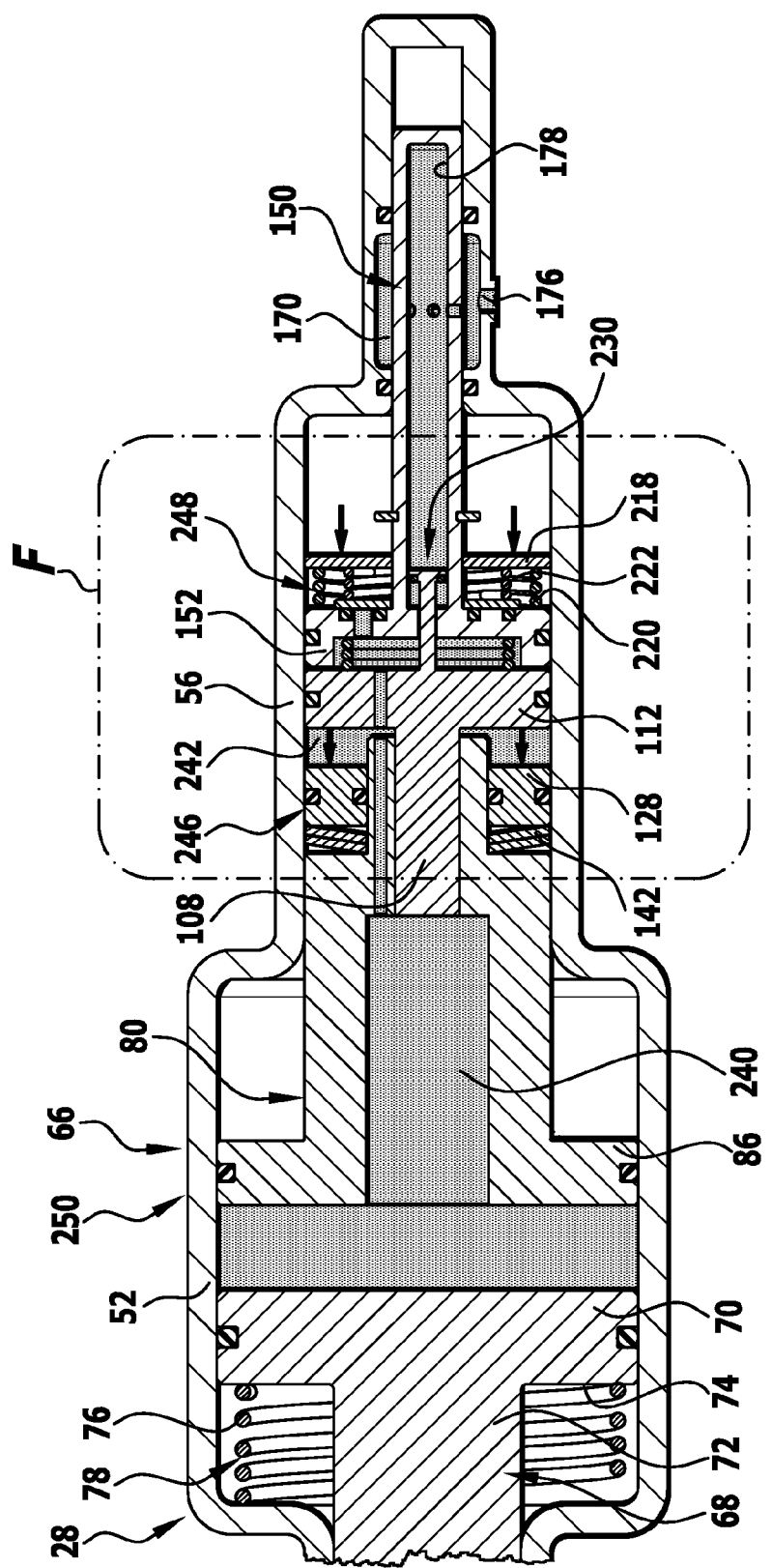

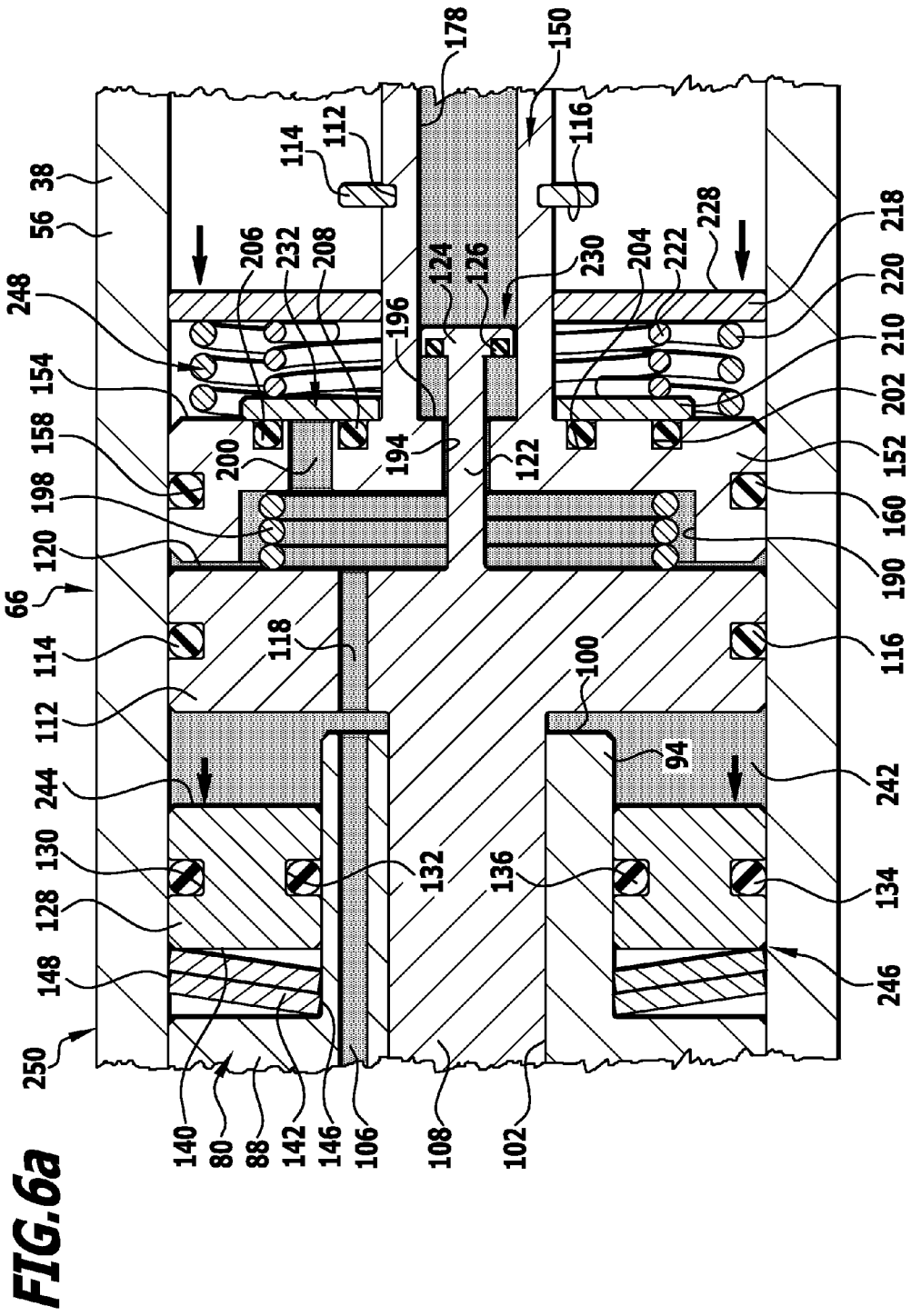

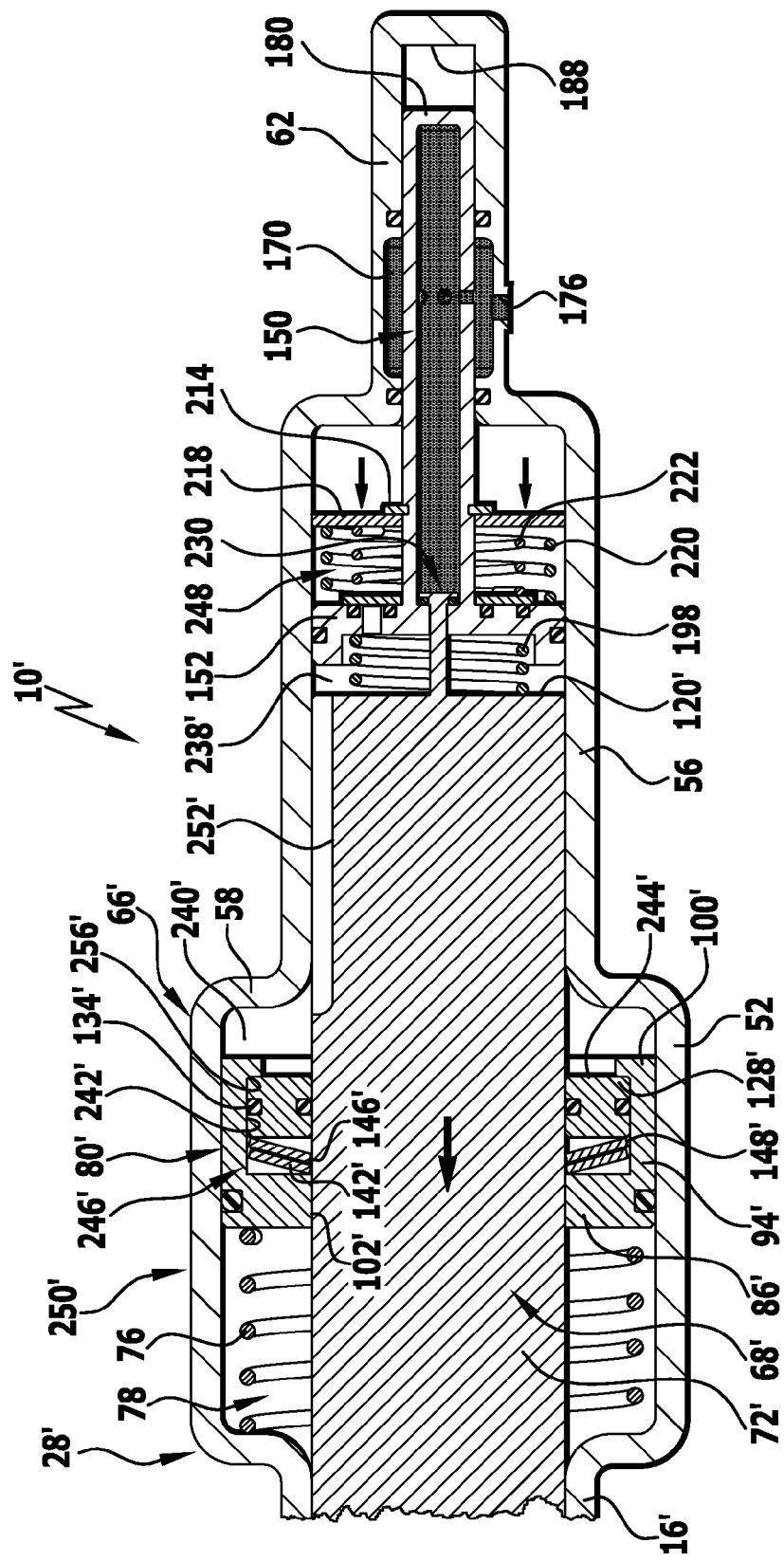

GAS-OPERATED SURGICAL INSTRUMENT

This application is a continuation of international application number PCT/EP2011/059647 filed on Jun. 10, 2011 and claims the benefit of German application number 10 2010 017 395.9 filed on Jun. 16, 2010, which are incorporated herein by reference in their entirety and for all purposes.

FIELD OF THE INVENTION

The present invention relates to a surgical instrument operated by pressurized gas generally, and more specifically to a surgical instrument operated by pressurized gas having a pressurized gas connection for connection to a source of pressurized gas, a working piston adapted to be acted upon by a pressurized gas, an actuating element for actuating the instrument, and a regulating device coupled to the actuating element and to the working piston for regulating a feed force of the working piston.

BACKGROUND OF THE INVENTION

Instruments of the kind described at the outset are known, for example, from US 2007/0213769 A1. They are, for example, configured in the form of pneumatic bone punches or as instruments for locking implants. To enable the instruments to be used independently of a source of pressurized gas, to which the instrument is connected via a hose, an instrument was proposed in DE 203 18 275 U1, in which a cartridge filled with a pressurized gas can be used as source of pressurized gas. However, a disadvantage of using a gas cartridge is that it can only make available a limited volume of gas, as a result of which use of the instrument is limited with respect to time or the number of actuating cycles.

It would, therefore, be desirable to provide a surgical instrument operated by pressurized gas that enables the largest possible number of actuating cycles or the longest possible actuating time with the lowest possible volume of pressurized gas.

SUMMARY OF THE INVENTION

In a first aspect of the invention, a surgical instrument operated by pressurized gas has a pressurized gas connection for connection to a source of pressurized gas, a working piston adapted to be acted upon by a pressurized gas, an actuating element for actuating the instrument, and a regulating device coupled to the actuating element and to the working piston for regulating a feed force of the working piston. The regulating device is configured such that for feed forces below a predetermined limit force it defines a first work area in which the working piston is movable in the distal direction solely owing to a feed force that can be applied with the actuating element. Above the limit force the regulating device defines a second work area in which the working piston is movable in the distal direction by being acted upon by pressurized gas.

BRIEF DESCRIPTION OF THE DRAWINGS

FIG. 3b shows an enlarged view of area B from FIG. 3a;
FIG. 3c shows an enlarged view of area C from FIG. 3a;
FIG. 4 shows a view in analogy with FIG. 3 in the first work area of the instrument;
FIG. 6 shows a view in analogy with FIG. 3 with the working piston being moved solely by being acted upon by pressurized gas in the second work area;
FIG. 6a shows an enlarged view of area F in FIG. 6;
FIG. 8a shows an enlarged view of the part of an alternative embodiment of the instrument comprising the pressure regulating device in the basic or initial position.

DETAILED DESCRIPTION OF THE INVENTION

Figure 1:
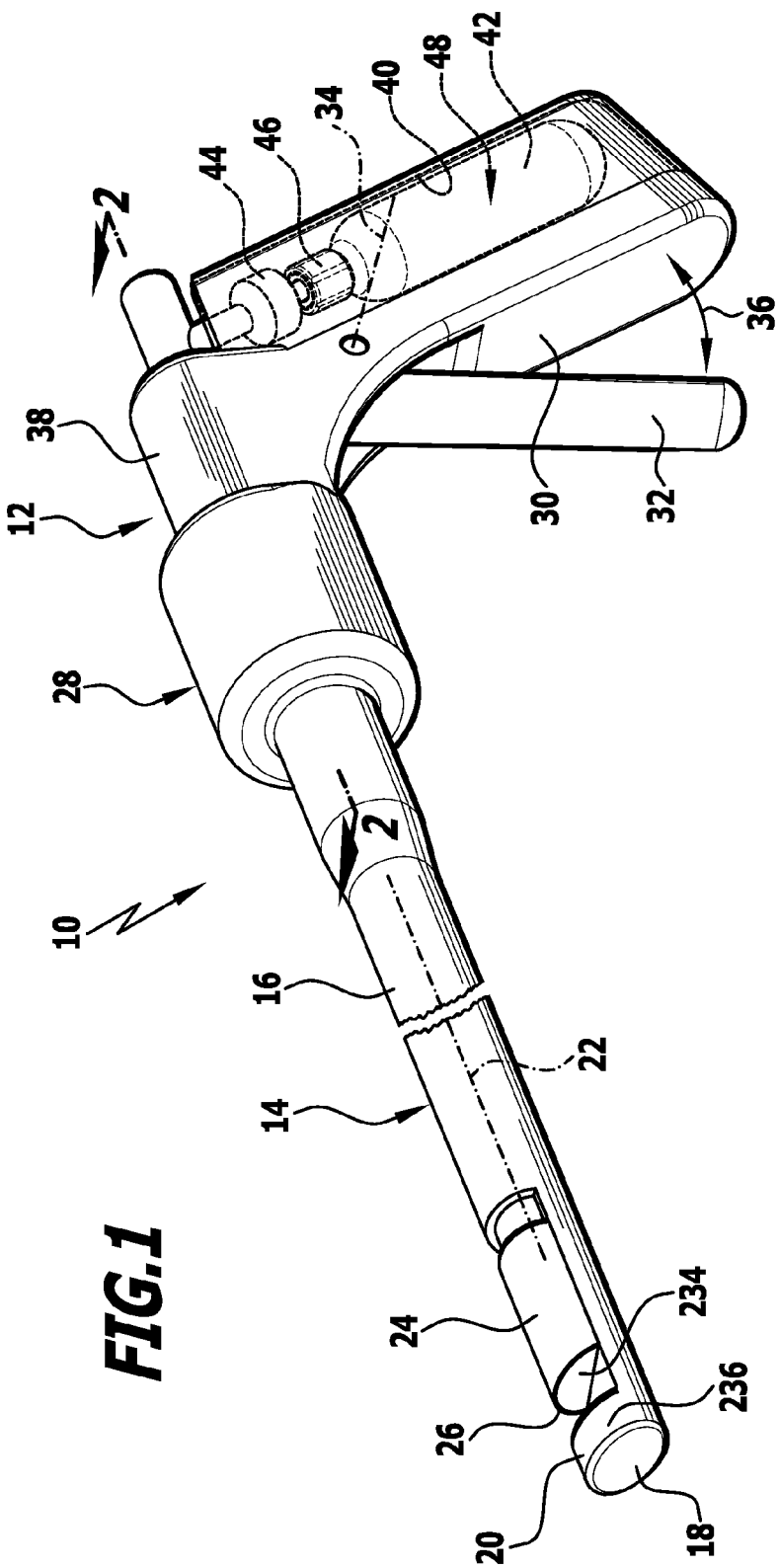
FIG. 1 shows a diagrammatic overall view of a surgical instrument in the form of a bone punch operated by pressurized gas.

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a surgical instrument operated by pressurized gas, having a pressurized gas connection for connection to a source of pressurized gas, a working piston adapted to be acted upon by a pressurized gas, an actuating element for actuating the instrument, and a regulating device coupled to the actuating element and to the working piston for regulating a feed force of the working piston, wherein the regulating device is configured such that for feed forces below a predetermined limit force it defines a first work area in which the working piston is movable in the distal direction solely owing to a feed force that can be applied with the actuating element, and wherein above the limit force the regulating device defines a second work area in which the working piston is movable in the distal direction by being acted upon by pressurized gas.

The proposed development of a surgical instrument operated by pressurized gas makes it possible to manage with as little pressurized gas as possible as source of outside energy. With the regulating device configured in accordance with the invention, pressurized gas is only used in the second or pneumatic work area in order to move the working piston if a certain limit force is exceeded. Below the limit force, the working piston is actuated solely owing to a manually introduced feed force. The proposed configuration of the instrument also has the advantage that the user, in spite of being assisted by the pressurized gas when actuating the instrument, can work tactilely with the instrument. The pressurized gas is only used when very high actuating forces have to be applied with the instrument, which is the case, for example, with bone punches or instruments for locking implants. Assistance of the pressurized gas is intentionally dispensed with in the first or mechanical work area for actuation paths of the working piston that are possible with only a low force, more specifically, a force below the limit force. In particular, when pressurized gas cartridges are used, it is thus possible to significantly increase the total number of actuating cycles possible, for example, in comparison with an instrument known from DE 203 18 275 U1.

In order to improve the tactility of the instrument for a user, it is advantageous if the regulating device is configured such that in the second work area a feed force acting on the working piston as a result of it being acted upon by pressurized gas is proportional to a feed force that can be applied with the actuating element. As the required actuating force that has to be applied by the working piston increases, the force perceptible by the user also increases. Owing to the proportionality of the feed force acting on the working piston as a result of it being acted upon by pressurized gas and the feed force that can be directly applied manually with the actuating element, a tactility is, however, also maintained for the user in the second work area above the defined limit force, more specifically, in an infinite manner. Optionally, it may also be advantageous if the regulating device is configured such that in the second work area a feed force acting on the working piston by it being acted upon by pressurized gas in combination or in interaction with a supporting element is proportional to a feed force that can be applied with the actuating element. In particular, in the first work area the supporting element can be decoupled from the working piston and movable relative to it, in the second work area it can be axially coupled to the working piston.

In order that the working piston can be acted upon by a pressurized gas in a simple way, it is advantageous if the regulating device comprises a work space adapted to be acted upon by pressurized gas, which is at least partially open in the direction towards the working piston. The pressurized gas introduced into the work space can thus act directly on at least part of the working piston and move the working piston when a limit pressure associated with the limit force is exceeded.

Advantageously, the working piston is displaceably guided in a working cylinder. In this way, a defined movement of the working piston relative to the instrument can be ensured.

In order to minimize losses of pressurized gas, it is advantageous if the working piston and the working cylinder are sealed relative to each other.

The instrument preferably comprises a supporting element which interacts with the working piston in the first and/or second work area. In particular, the working piston can be supported on and/or coupled to the supporting element in at least one of the work areas. As a result, in particular, a purely mechanically actuatable work area can be decoupled from a work area operated solely by pressurized gas. Alternatively or additionally, by coupling the supporting element and the working piston, it is, in particular, possible to alter an effective area for the pressurized gas, for example, to increase it in the coupled state. As a result, a feed force increase can, for example, be additionally activated in the transition from a first to a second work area of the instrument.

In order that the working piston can be displaced in a simple way directly by introducing a manual actuating force, it is advantageous if the working piston is supported in the first work area on the supporting element. For example, when the supporting element moves in the distal direction, the working piston supported on it can also be moved in the distal direction.

Preferably, the working piston is coupled in the second work area to the supporting element. For example, by coupling the supporting element to the working piston, an effective area for the pressurized gas can be increased, so that in the coupled state, for example, a feed force can be increased, additionally activated, so to speak, by appropriate action of pressurized gas. In particular, the working piston can be decoupled in the first work area from the supporting element.

A particularly compact design of the instrument can be achieved by the work space being formed on the supporting element. In particular, with a supporting element that is arranged so as to be movable, the work space can then "move with it", so that only the volume of the work space defined on the supporting element has to be acted upon with pressurized gas in a first step in order to move the working piston in the distal direction away from the supporting element.

Manual actuating forces applied via the actuating element can thus be transmitted directly from the supporting element to the working piston if the working piston is supported in the first work area directly on the supporting element.

Actuation of the working piston by pressurized gas can be dispensed with, in particular, if the supporting element is movable in the distal direction in the first work area solely owing to the feed force that can be applied with the actuating element.

For optimum interaction between the supporting element and the working piston, it is advantageous if the supporting element is guided at least in some sections in the working cylinder, and if the supporting element and the working cylinder are sealed relative to each other. The supporting element can thus be moved in a defined manner at least partially in the working cylinder and guided by it without pressurized gas being able to escape. Optionally or alternatively, it may also be advantageous if the working piston and the supporting element are displaceably guided relative to each other or on each other and are sealed from each other, for example, with a sealing element, preferably in the form of a sealing ring, arranged, formed or held on the working piston and/or on the supporting element.

In order to further assist and enable in a defined manner movement of the supporting element, it is advantageous if the instrument further comprises a guiding device for guiding movement of the supporting element in the distal and proximal directions.

The construction of the instrument is particularly straightforward if the guiding device comprises a guiding cylinder in which the supporting element is displaceably guided. In particular, the supporting element may be of piston-like configuration in the area in which it is displaceably guided in the guiding cylinder.

In order that as little pressurized gas as possible can escape from the instrument, it is advantageous if the supporting element and the guiding device are sealed relative to each other.

In accordance with a further preferred embodiment of the invention, it may be provided that the regulating device comprises a locking device for temporarily securing the supporting element in the second work area. With the locking device it is, for example, possible to temporarily secure the supporting element relative to the working cylinder and/or to the guiding cylinder, so that the working piston can then only be moved in the distal direction by being acted upon by pressurized gas. The possibility of securing the supporting element, in particular, only in the second work area to the instrument allows the appropriate amount of pressurized gas to be accessed and used to feed the working piston only when high working forces are actually required.

The supporting element can be temporarily secured to the instrument in a particularly simple way if the locking device comprises at least one locking member for temporarily securing the supporting element to the guiding device or to the working piston. Optionally, it also conceivable to configure the locking device such that the supporting element can be temporarily secured to the working cylinder.

The construction and manufacture of the instrument can be further simplified if the at least one locking member is configured in the form of a latching and/or clamping element. The clamping element can become effective, in particular, when the predefined limit force is exceeded. Furthermore, a locking mechanism can be formed in a simple way by a latching connection with latching members corresponding to and interacting with one another.

To temporarily secure the supporting element in a defined and simple way on the instrument, it is advantageous if the clamping element is supported, on the one hand, on the supporting element and, on the other hand, on the guiding device or on the working piston. A direct clamping of the supporting element by means of the clamping element on the guiding device or on the working piston can thus be achieved, more specifically, preferably in the second work area.

Particularly simple actuation of the locking member can be achieved by the locking device comprising a piston element adapted to be acted upon by pressurized gas, which is movable in the distal direction by being acted upon by pressurized gas and is pressable against the at least one locking member to clamp the at least one locking member relative to the supporting element and relative to the guiding device or relative to the working piston. Furthermore, this special configuration makes it possible to simultaneously use the pressurized gas usable for moving the working piston to secure the supporting element on the instrument, in particular, on the guiding device or on the working piston, more specifically, in dependence upon the pressurized gas prevailing in the instrument. In particular, clamping of the at least one locking member relative to the supporting element and relative to the guiding device or relative to the working piston can take place in a self-locking manner, and by making use of the principle of recoil, clamping of the interacting parts is all the stronger, the stronger the prevailing counter pressure.

A defined movement of the piston element on the instrument can be achieved, in particular, by the piston element being held and guided on the supporting element and/or on the guiding device or on the working piston. A defined movement of the piston element relative to the supporting element and relative to the guiding device or relative to the working piston can thus be ensured.

To avoid further losses of pressurized gas, it may, furthermore, be advantageous if the piston element and the guiding device and/or the working piston are sealed relative to each other. Furthermore, it is advantageous if the piston element and the supporting element are sealed relative to each other so as to also avoid losses of pressurized gas here.

It is advantageous if the actuating force introduced via the actuating element is transmittable to an actuating member mounted so as to be movable parallel to the working piston. This makes it possible, owing to the introduced actuating force, to move the actuating member in the distal direction, too, i.e., in the direction towards the working piston, in order to move the working piston in the distal direction.

In accordance with a further preferred embodiment of the invention, it may be provided that the regulating device comprises a pressure regulator for regulating a gas pressure acting on the working piston in dependence upon an actuating force introducible via the actuating element. The pressure regulator makes it possible, in particular, to fix the limit force which defines and separates the first and second work areas from each other. In particular, the pressure regulator can be configured such that the pressure prevailing in the pressurized gas in the instrument can only move the working piston above the predefined limit force.

The pressure regulator is preferably configured to regulate the gas pressure acting on the working piston in dependence upon the actuating force acting on the actuating member. Independently of a configuration of the actuating element, the gas pressure is, therefore, only regulated in dependence upon the actuating force actually acting on the actuating member.

The construction of the instrument may be further simplified if the pressure regulator comprises a valve which in the first work area is closed. The pressure regulator thus prevents the working piston from being able to be acted upon in the first work area by pressurized gas with sufficient working pressure to move the working piston.

The pressure regulator preferably comprises a first pressure member for defining an opening force required to open the valve. The type and configuration of the pressure member thus enable the limit force that has to be exceeded in order to open the valve to be directly preset.

A particularly compact arrangement and configuration of the regulating device can be achieved, in particular, by the first pressure member being supported, on the one hand, on the pressure regulator and, on the other hand, on the supporting element or on the working piston. In this way, the first pressure member can act directly on the pressure regulator, optionally also on the valve.

To enable positioning of the pressure regulator in dependence upon a position of the supporting element on the instrument, it is advantageous if the pressure regulator comprises a pressure regulating piston element which is displaceably guided in the guiding device.

To avoid losses of pressurized gas, it is advantageous if the pressure regulating piston element and the guiding device are sealed relative to each other.

The regulating device advantageously comprises a second pressure member for transmitting an actuating force from the actuating member to the pressure regulator. The second pressure member may, in particular, be deformable in dependence upon an actuating force acting upon it and may be used for transmitting the introduced actuating force from the actuating member to the pressure regulator.

Furthermore, it may be advantageous if the regulating device comprises a third pressure member for transmitting an actuating force from the actuating member to the pressure regulator. Two different force ranges can thus be defined by the second and third pressure members independently of each other. The third pressure member may, in particular, be a further pressure member. The provision of the second pressure member defined above is not compulsory, but optional. Furthermore, the third pressure member may also be arranged and configured such that with it an actuating force can be directly transferred to a ventilation valve comprised by the pressure regulator.

To enable pressurized gas to be removed from the work space in a defined manner, it is advantageous if the regulating device comprises a ventilation valve for ventilating the work space.

In order that the instrument can be configured even more compactly, it is advantageous if the pressure regulator comprises the ventilation valve.

The pressure starting from which the ventilation valve opens can be set in a simple way by the ventilation valve being openable counter to the action of the third pressure member. An opening force for opening the ventilation valve can thus be defined directly with the third pressure member.

In order to keep the size of the instrument as compact as possible, the pressure regulating piston element preferably comprises the ventilation valve or a part thereof.

The work space can be flooded with pressurized gas in a defined manner if the first, second and third pressure members are arranged such that a force applied by the first pressure member counteracts the forces applied by the second and third pressure members. The arranging of the pressure members in such a way makes it possible to introduce an actuating force via the second and third pressure members, and when the force applied by the second and third pressure members is somewhat greater than the counteracting force of the first pressure member, the valve is openable to allow the pressurized gas to flow into the work space.

To enable the working piston to be moved in the first work area without it being acted upon by pressurized gas, it is advantageous if the first, second and third pressure members are configured such that a force applied by the first pressure member in the first work area is always greater than the sum of the forces applied by the second and third pressure members. In particular, this prevents the valve from being openable to establish a fluid connection between the work space and the source of pressurized gas.

In accordance with a further preferred embodiment of the invention, a resetting device may be provided for transferring the instrument from a working position into which the working piston has been moved in the distal direction back into a basic position in which the working piston assumes its most proximal position. If an operator puts the instrument down, it is thus possible to automatically bring the instrument back into its basic position again. In particular, the resetting device may be configured in the form of a pneumatic resetting device, in accordance with which it may be provided that the working piston is moved back into the basic position by being appropriately acted upon by overpressure or underpressure.

The construction of the resetting device is particularly straightforward if it comprises at least one resetting member which is supported, on the one hand, on the guiding device and, on the other hand, on the working piston and/or on the supporting element for applying a force acting in the proximal direction to the working piston and/or the supporting element. In particular, it may be supported on the distal side on the working cylinder and on the proximal side on the working piston, so that a resetting force acting in the proximal direction can be applied to the working piston by the resetting member if the working piston has been moved from its most proximal position in the distal direction. Optionally, in particular, also alternatively, it can be supported on the distal side on the working cylinder and on the proximal side on the supporting element, so that a resetting force acting in the proximal direction can be applied to the supporting element by the resetting member if the supporting element has been moved from its most proximal position in the distal direction.

The instrument preferably comprises a housing, and the pressurized gas connection and/or the working piston and/or the actuating element and/or the regulating device are arranged or formed on or in the housing. In particular, the aforementioned components of the instrument can be arranged so as to be protected or at least partially protected in the housing.

To improve the handling of the instrument, it is advantageous if the housing comprises a gripping area and if the actuating element is arranged or formed or mounted on the gripping area. An operator can thus grasp the instrument at the gripping area and simultaneously operate the actuating element with the same hand.

Preferably, the gripping area comprises a pressurized gas container receptacle for a pressurized gas container, and the pressurized gas connection is arranged or formed in the area of or in or on the pressurized gas container receptacle. This allows the pressurized gas container to be arranged in a compact and ergonomically optimized manner on the instrument. In particular, the pressurized gas container receptacle may be closeable, so that the pressurized gas container can be arranged so as to be fully protected on the instrument.

The surgical instrument, as described above, may, in particular, also be configured in the form of an instrument grip. To enable surgery to be performed with the instrument, it is advantageous if a surgical tool element is arranged at a distal end of the working piston.

For example, to enable tissue or bone to be worked on with the instrument, it is advantageous if the surgical tool element is configured in the form of a cutting edge.

In order that the instrument can be used again, even if the surgical tool element has become damaged and can no longer be repaired, it is advantageous if the tool element is adapted for releasable connection or temporary coupling to the working piston. In accordance with the specific purpose or the requirements, the optimally suited tool element can then be coupled to the working piston when the tool element has become worn.

In principle, it is conceivable to connect the surgical instrument via a pressurized gas connection to a source of pressurized gas, for example, a pressurized gas supply system in a hospital. To enable the instrument to be used in an independent manner and, in particular, in a hose connection-free manner, i.e., without any interfering connection hoses that connect the instrument to the source of pressurized gas, it is advantageous if the source of pressurized gas is a gas container filled with a pressurized gas, and if the gas container is releasably connectable to the pressurized gas connection. This allows the empty gas container to be removed from the instrument and replaced by a full gas container, when required.

The instrument preferably comprises a source of pressurized gas in the form of a pressurized gas container. Provided the pressurized gas container is filled with the pressurized gas, an instrument that is immediately ready for use can then be made available, with which the working piston can be moved in the distal direction in the first work area without the assistance of pressurized gas and in the second work area with the assistance of pressurized gas.

The instrument is preferably configured in the form of a bone punch. Bone punches often require very high forces, for example, in the order of magnitude of 750 newtons, for working on, for example, severing, bone or tissue. Bone punches comprise two interacting tool members, namely an anvil part and a cutting edge which can be moved relative to the anvil part. Typically, the anvil part is connected to the housing of the instrument, and the cutting edge is preferably releasably connectable to the working piston of the instrument so that it can be exchanged, when required. In particular, in bone punches, a maximum path of displacement is predetermined by the construction of the instrument. It corresponds to a spacing of the cutting edge from the anvil part in the basic position. If there is no tissue located between the cutting edge and the anvil part, a high force is not required to move the cutting edge in the direction towards and against the anvil part. In this case, there is no necessity for pressurized gas application. If, however, tissue or bone is located between the cutting edge and the anvil part, a high working force is then required if the cutting edge and the anvil part are to clamp the bone or the tissue between them and sever it. Only then, owing to the special configuration of the instrument, is pressurized gas used to apply the working force required to work on the bone or the tissue. A pressurized gas consumption can thus be minimized by the regulating device as there is no necessity for the working piston to be acted upon by pressurized gas on the displacement path of the tool element on which it does not have to apply any force.

In accordance with an alternative preferred embodiment of the invention, the instrument may be configured in the form of an implant locking instrument. Similarly to a bone punch, with an implant locking instrument, too, a high working force only actually has to be applied on a relatively short path or stroke range of the working piston, in order, for example, to move, in particular, spread, implant parts relative to each other. Only in the second work area is pressurized gas then actually used to act upon the working piston with the necessary force, which would only be possible with difficulty or would not be possible at all by manual application of force with the actuating element.

The following description of preferred embodiments of the invention serves for a more detailed explanation in conjunction with the drawings.

A surgical instrument is diagrammatically represented and generally designated by reference numeral 10 in FIG. 1. It is configured in the form of a bone punch and comprises a handle 12 and a shaft part 14 connected, optionally, also releasably connectable, to the handle 12, and having a shaft 16 fixed relative to the handle 12 or fixable in a rotationally fixed manner to the handle 12. An anvil part 20 is formed at the distal end 18 of the shaft 16 in the form of a projection extending substantially transversely to a longitudinal axis 22 defined by the shaft 16. The projection forms an abutment for a cutting edge 26 which forms a distal end of a punch part 24 displaceably mounted in the shaft 16. The cutting edge 26 can be pressed against the anvil part 20 to work on bone and/or tissue.

The handle 12, which may also perform the function of a surgical instrument in accordance with the invention without the shaft part 14, for example, as an implant locking instrument in order to move two implant parts relative to each other, comprises a drive part 28 of substantially rotationally symmetrical configuration, which extends as an extension of the longitudinal axis 22 when the shaft part 14 is connected to the handle 12. At a proximal end of the drive part 28, a gripping area 30 protrudes transversely therefrom. An actuating element 32 in the form of a lever pivotable about a pivot axis 34 oriented transversely to the longitudinal axis 22 is pivotably mounted on the gripping area 30. The lever can be pivoted by an operator in the direction of arrow 36 towards the gripping area 30.

The gripping area 30 forms together with the drive part 28 a housing 38 on which is formed, as represented only diagrammatically in FIG. 1, a pressurized gas container receptacle for receiving a pressurized gas container 42. The pressurized gas container receptacle 40 is integrated in the gripping area 30. A pressurized gas connection 44, which is engageable with and connectable in a gas-tight manner to a corresponding connection piece 46 of the pressurized gas container 42 forming a source of pressurized gas 48, is formed in the pressurized gas container receptacle 40. Optionally, it is possible for the gripping area 30 to be of slimmer configuration, as shown by way of example in FIG. 2, and for the pressurized gas container receptacle 40 to be dispensed with completely. The instrument 10 is also optionally connectable to a source of pressurized gas via a pressurized gas hose 50. This allows the instrument 10 to also be used without the use of a pressurized gas container 42 by it being connected, for example, to a pressurized gas supply, as is usually provided in a hospital.

The core piece of the instrument 10 is the drive part 28. It comprises a working cylinder 52, which adjoins the shaft 16 at the proximal side, and the internal diameter of which is somewhat greater than twice the size of an internal diameter of the shaft 16. The shaft 16 and the working cylinder 52 are connected to each other by a flange 54 protruding radially from the longitudinal axis 22. At the proximal side, the working cylinder 52 is adjoined by a guiding cylinder 56, which is connected to the working cylinder 52 by a further flange 58 extending in the radial direction. An internal diameter of the guiding cylinder 56 is smaller than an internal diameter of the working cylinder 52, but somewhat larger than the internal diameter of the shaft 16. Connected to the guiding cylinder 56 at the proximal side by a further flange 60 extending in the radial direction away from the longitudinal axis 22 is a bearing cylinder 62 which is closed at the proximal side by an end wall 64. The internal diameter of the shaft 16 is about two and a half times larger than the internal diameter of the bearing cylinder 62. The working cylinder 52, the guiding cylinder 56 and the bearing cylinder 62 form a part of the housing 38 and a guiding device designated in its entirety by reference numeral 250. They also serve to receive the drive of the instrument 10 and a regulating device designated in its entirety by reference numeral 66.

A working piston 68, which comprises a piston disc 70 and a cylinder section 72, formed integrally with the piston disc 70 and extending in the distal direction, is held and guided in the working cylinder 52. The external diameter of the solid cylinder section 72 corresponds to the internal diameter of the shaft 16. The cylinder section 72 may be formed integrally with the punch part 24. Optionally, the cylinder section 72 may also be detachable from the punch part 24 by means of a coupling device, not shown, in order to exchange the punch part 24 as required. An external diameter of the piston disc 70 corresponds to the internal diameter of the working cylinder 52.

Figure 2:
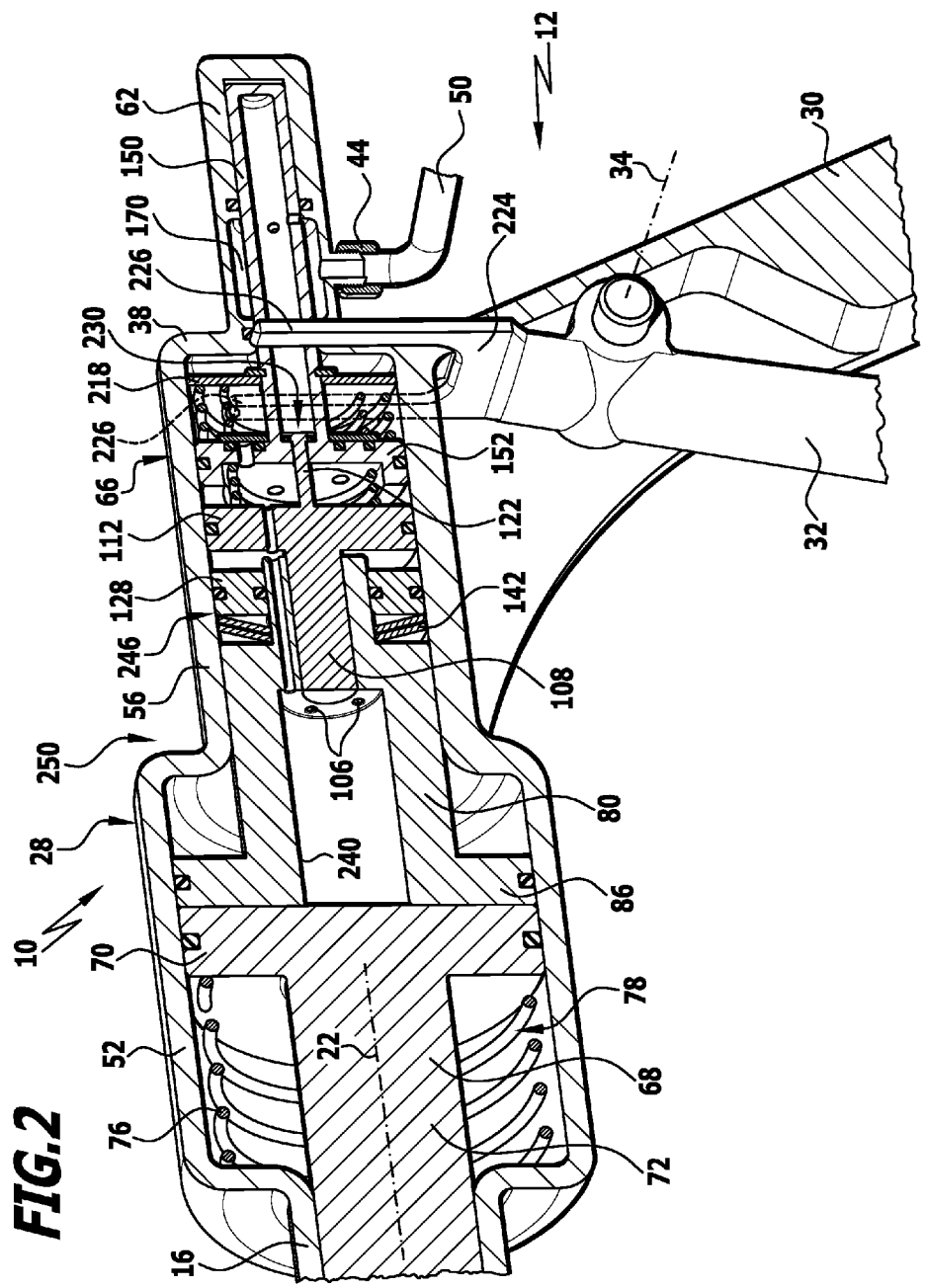
FIG. 2 shows a sectional view taken along line 2-2 in FIG. 1.
Figure 3:
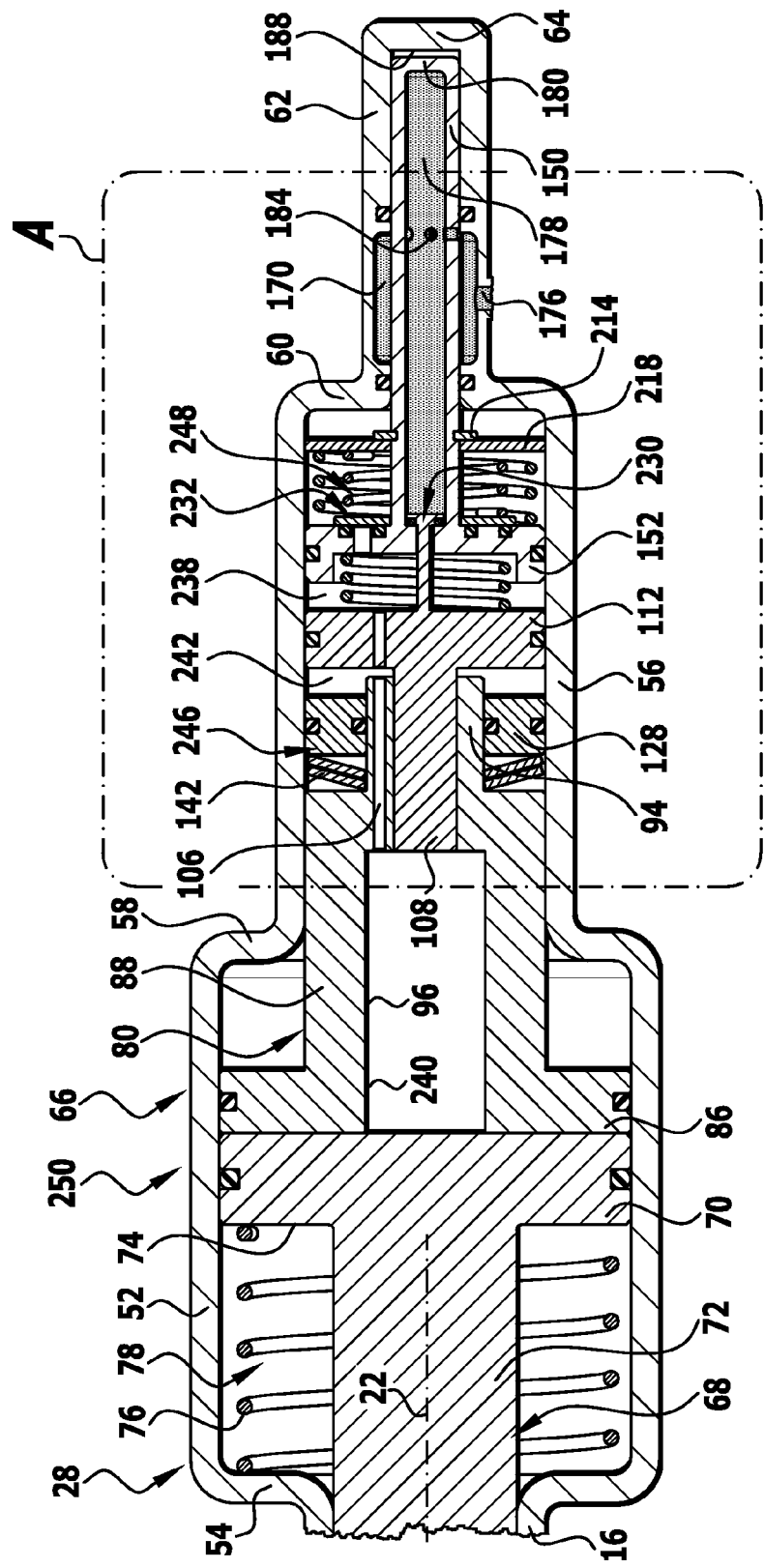
FIG. 3 shows an enlarged view of the part of the instrument comprising the pressure regulating device in the basic or initial position.
Figure 3A:
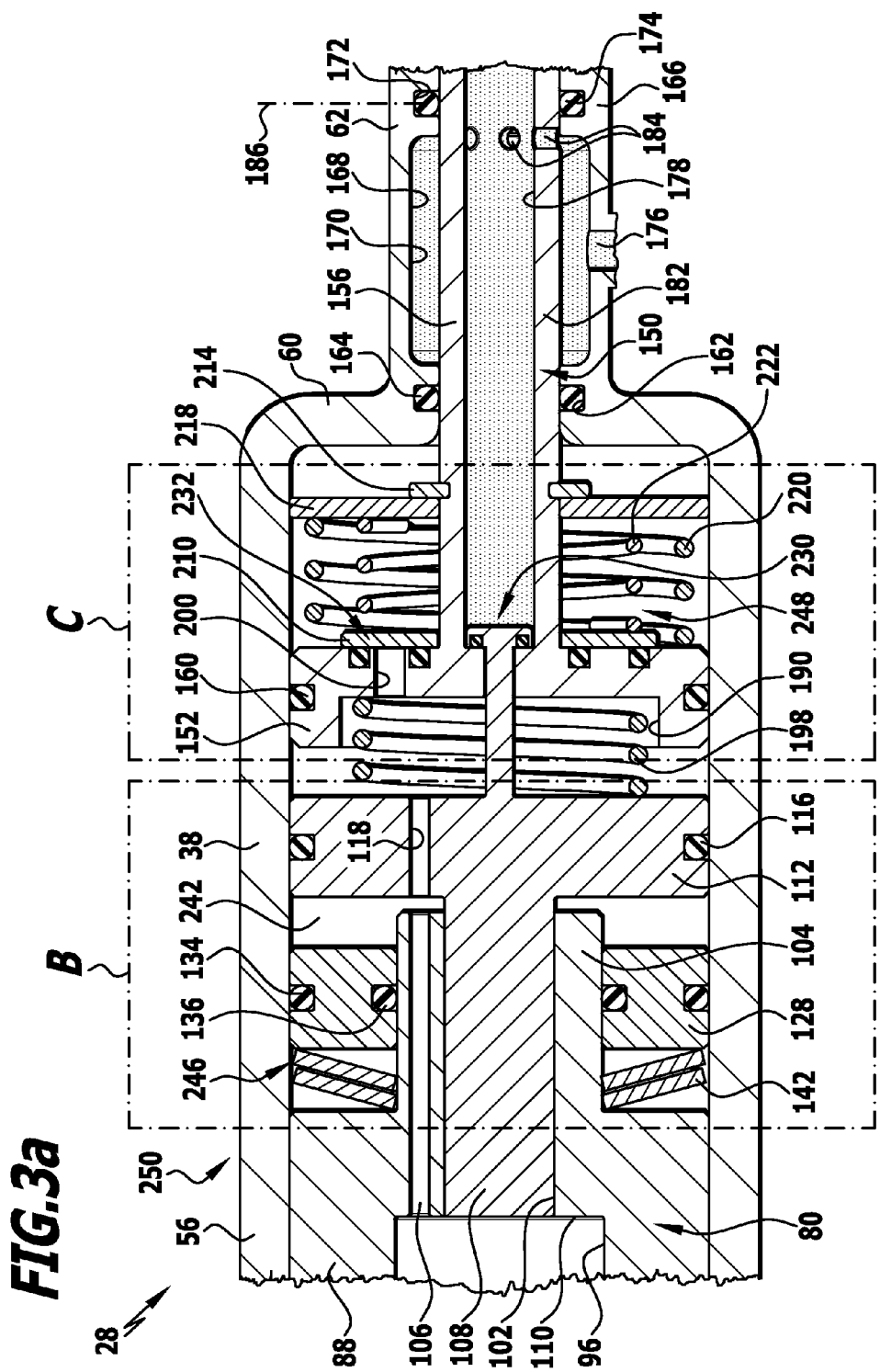
FIG. 3a shows an enlarged view of area A from FIG. 3.
Figure 3B:
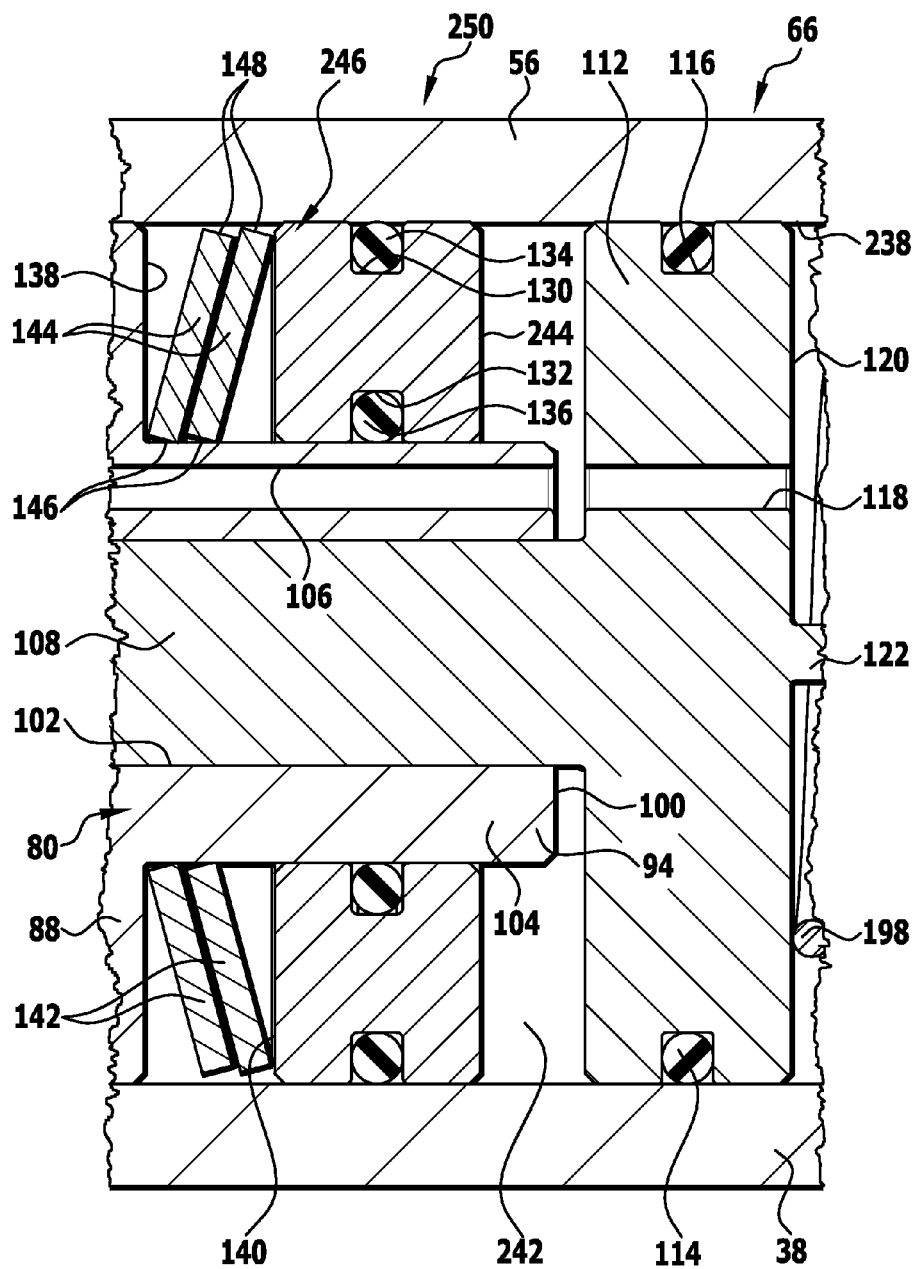
Figure 3C:
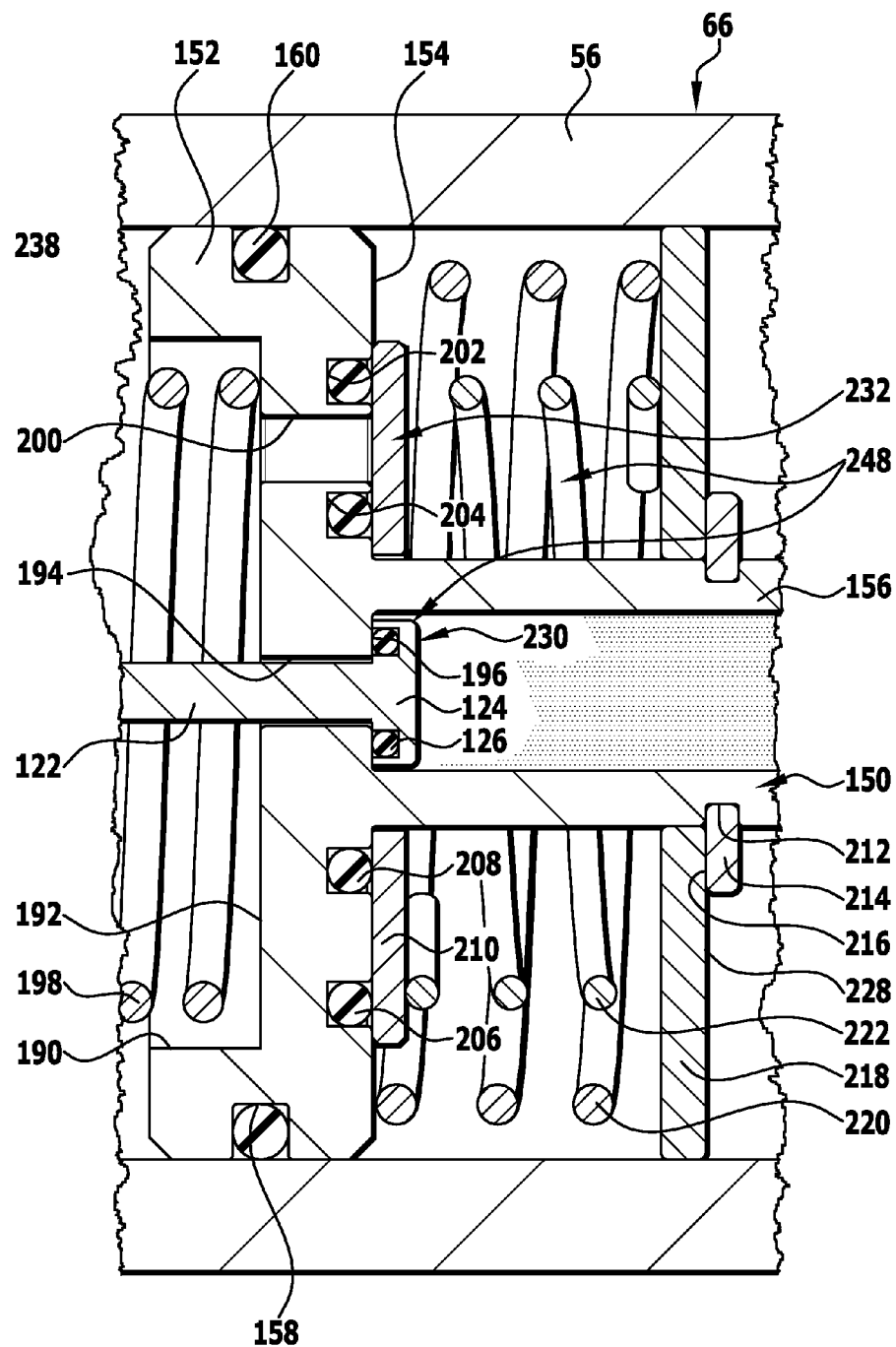

A helical spring forming a resetting member 76 is supported on an annular face 74, facing in the distal direction, of the piston disc 70. At the distal side, the resetting member 76 is supported on the inside on the flange 54. The resetting member 76 is configured as a pressure member and forms part of a resetting device 78, which moves the working piston 68, if no actuating forces introduced or required by a user are acting on it, into its basic position, i.e., in the proximal direction until it lies against a supporting element 80, as shown in FIGS. 2 and 3. The working piston 68 is, therefore, displaceably guided in the working cylinder 52 and in the shaft 16, and, consequently, at least partially by the guiding device 250, parallel to the longitudinal axis 22 in the distal and proximal directions. A sealing element 84 in the form of an O-ring is inserted in an annular groove 82, formed on an outer surface facing way from the longitudinal axis 22, of the piston disc 70, in order to seal the working piston 68 and the working cylinder 52 relative to each other.

The supporting element 80 is configured in the form of a piston with a piston disc 86 forming a distal end of the supporting element 80. The piston disc 86 is formed integrally with a cylinder section 88 extending in the proximal direction. An external diameter of the piston disc 86 corresponds to the internal diameter of the working cylinder 52. An external diameter of the cylinder section 88 corresponds to the internal diameter of the guiding cylinder 56. A sealing element 92 in the form of an O-ring is inserted in an annular groove 90, formed on an outer surface facing away from the longitudinal axis 22, of the piston disc 86, in order to seal the supporting element 80 and the working cylinder 52 relative to each other. Protruding from the cylinder section 88 at the proximal side is a short, sleeve-shaped cylinder section 94, which is aligned coaxially with the longitudinal axis 22. An external diameter of the cylinder section 94 is about 1.5 times larger than an internal diameter of the bearing cylinder 62.

A blind hole 96, which is open facing in the distal direction, is formed coaxially with the longitudinal axis 22 in the cylinder section 88. The internal diameter of the blind hole 96 corresponds to the external diameter of the cylinder section 94 and is, therefore, smaller than the internal diameter of the shaft 16. A proximal end 100 of the cylinder section 94 is connected to the blind hole 96 via a bore 102 extending coaxially with the longitudinal axis 22. A plurality of bores 106 distributed uniformly over the circumference of the cylinder section 94 and extending parallel to the longitudinal axis 22 are formed in a remaining cylinder wall 104 of the cylinder section 94 and also connect the end 100 to the blind hole 96.

A bolt section 108, which terminates at the distal side flush with a bottom 110, facing in the distal direction, of the blind hole 96, is inserted in the bore 102. The bolt section 108 is somewhat longer than the bore 102 and is integrally connected at the proximal side to a further piston disc 112, the external diameter of which corresponds to the internal diameter of the guiding cylinder 96. The piston disc 112 is, therefore, spaced somewhat from the proximal end 100 of the cylinder section 94. A sealing element 116 in the form of an O-ring is inserted in an annular groove 114, formed on an outer surface, facing away from the longitudinal axis 22, of the piston disc 112, in order to seal the piston disc 112 and the guiding cylinder 56 relative to each other.

Coaxially with the bores 106, bores 118 are provided in the same number and with the same internal diameter on the piston disc 112 and are aligned flush with the bores 106. The bolt section 108 may be glued into the opening 102. Optionally, the blind hole 96 may be provided with an internal thread, the bolt section 108 with a corresponding external thread, so that the bolt section 108 and the supporting element 80 can be screwed to each other. In any case, the bolt section 108 is immovably connected to the cylinder section 94.

A cylindrical valve pin 122 facing in the proximal direction protrudes coaxially with the longitudinal axis 22 from a proximal end face 120 of the piston disc 112. Formed on a proximal end of the valve pin 122 is an annular flange 124 on which is held a sealing element 126, which is inserted in an annular groove facing in the distal direction.

A clamping piston 128 is guided on the cylinder section 94 parallel to the longitudinal axis 22. It comprises two annular grooves 130 and 132, which are open facing in the radial direction away from the longitudinal axis 22 and in the radial direction towards the longitudinal axis 22, respectively. Sealing elements 134 and 136 in the form of O-rings are inserted in the annular grooves 130 and 132 in order to seal the clamping piston 128 and the guiding cylinder 56 and the clamping piston 128 and the cylinder section 94, respectively, relative to each other.

Two identical clamping elements 142 in the form of discs 144 are arranged between an annular face 138, facing in the proximal direction, of the cylinder section 88 and an annular face 140, facing in the distal direction, of the clamping piston 128. It is, of course, possible to also provide more than two clamping elements, which, furthermore, do not have to be of identical design. The discs 144 do not define a plane perpendicular to the longitudinal axis 22, but are inclined somewhat relative to the longitudinal axis 22. Inner edges 146 of the discs 144, which face in the radial direction towards the longitudinal axis 22, are thus arranged somewhat more distally than outer edges 148 of the discs 144, which face away from the longitudinal axis 22. The more distal disc 144 preferably lies, adjacent to the inner edge 146, against the annular face 138, and the proximal disc 144, adjacent to its outer edge 148, against the annular face 140.

The regulating device 66 further comprises a pressure regulating piston 150, which comprises a piston disc 152 and a cylinder section 156 protruding from a side face 154, facing in the proximal direction, of the piston disc 152. The piston disc 152 has an external diameter which corresponds to the internal diameter of the guiding cylinder 56. A sealing element 160 in the form of an O-ring is inserted in an annular groove 158, formed in an outer surface facing away from the longitudinal axis 22, of the piston disc 152, in order to seal the piston disc 152 and the guiding cylinder 56 relative to each other. The cylinder section 156 has an external diameter which corresponds to the internal diameter of the bearing cylinder 62.

An annular groove 162, open in the direction towards the longitudinal axis 22, in which is inserted a sealing element 164 in the form of an O-ring, is formed on the guiding cylinder 56 in the region of the flange 58 in order to seal the cylinder section 156 and the guiding cylinder 56 relative to each other. Spaced somewhat from the annular groove 162 on the proximal side thereof, an annular groove-like recess 168 extending in the direction of the longitudinal axis 22 is formed in an annular wall 166 forming the bearing cylinder 62. The annular groove-like recess 168 defines an annular space 170 surrounding the cylinder section 156. In analogy with the annular groove 162, a further annular groove 172 is formed on the proximal side of the recess 168 and spaced somewhat therefrom. A sealing element 174 in the form of a further O-ring is inserted in the annular groove 172 in order to seal the cylinder section 156 and the bearing cylinder 62 relative to each other on the proximal side of the annular space 170. The pressurized gas connection 44, which in the form of a sleeve-shaped connection piece, protrudes vertically to the longitudinal axis 22 from the outside of the bearing cylinder 62, is connected to the annular space 170 via a bore 176, the longitudinal axis of which is oriented perpendicularly to the longitudinal axis 22.

The cylinder section 156 is hollow and defines an elongate, hollow-cylindrical inner space 178, which extends from an end wall 180 of the cylinder section 156 at the proximal side to the piston disc 152. A sleeve-shaped remaining wall 182 of the cylinder section 156 is provided with a plurality of bores 184, which are distributed over the circumference of the wall 182, and the longitudinal axes of which intersect the longitudinal axis 22 perpendicularly. All bores 184 are arranged in a plane 186 which is oriented perpendicularly to the longitudinal axis 22. Furthermore, the bores 184 are positioned on the cylinder section 156 such that they are in fluid connection with the annular space 170 even when the end wall 180 lies against an end face 188, facing in the distal direction, of the end wall 64. The extent, i.e., a length of the annular space 170 parallel to the longitudinal axis 22 is selected such that the bores 184 are still in fluid connection with the annular space 170 when the cylinder section 156 assumes its most distal position, i.e., is displaced to the maximum extent in the distal direction. It is thus possible, independently of a position of the cylinder section 156 relative to the bearing cylinder 62, for pressurized gas to pass from the source of pressurized gas 48 via the pressurized gas connection 44 into the inner space 178.

A flat blind hole 190 facing in the distal direction is formed in the piston disc 152. A bore 194 formed coaxially with the longitudinal axis 22 penetrates a bottom 192 of the blind hole 190. The internal diameter of the bore 194 is somewhat larger than an external diameter of the valve pin 122 which penetrates the bore 194. An internal diameter of the inner space 178 is somewhat larger than an internal diameter of the bore 194. An external diameter of the annular flange 124 is somewhat smaller than an internal diameter of the inner space 178. The annular flange 124 can be brought into abutment with the side face 154, more particularly, with a part thereof, namely an annular face 196 facing in the proximal direction, which surrounds the bore 194 and delimits the inner space 178. The annular flange 124 and the piston disc 152 can be sealed relative to each other by the sealing element 126.

A first pressure member 198 in the form of a helical spring is supported on the distal side on the end face 120 and on the proximal side on the bottom 192 and presses the piston disc 152 in the proximal direction against the annular flange 124. The bore 194 is then closed.

A further bore 200, which connects the bottom 192 and the side face 154 with each other, is provided on the piston disc 152 parallel to the bore 194, but spaced from it in the radial direction. Two annular grooves 202 and 204, which are open facing in the proximal direction, are formed concentrically with the longitudinal axis 22 in the side face 154. They are arranged such that the annular groove 202 is spaced somewhat further in the radial direction from the longitudinal axis 22 than the bore 200, and the annular groove 204 is arranged somewhat closer to the longitudinal axis 22 than the bore 200. Sealing elements 206 and 208 in the form of O-rings are inserted in the annular grooves 202 and 204 and interact with a valve disc 210 surrounding the cylinder section 156 in order to close the bore 200 in a gas-tight manner. The valve disc 200 defines a plane perpendicular to the longitudinal axis 22.

A flat, narrow annular groove 212 is formed on an outer side of the cylinder section 56, more particularly, at a spacing from the side face 154, which is somewhat less than an extent of the annular space 170 parallel to the longitudinal axis. A disc 214 having an external diameter which is less than an external diameter of the bearing sleeve 62 and defining an annular stop surface 216 facing in the distal direction is inserted in the annular groove 212. The disc 214 may simultaneously serve as stop for delimiting movement of the cylinder section 156 in the proximal direction, namely when the disc 214 strikes the flange 60. Between the disc 214 and the side face 154, an actuating member 218 in the form of a flat disc is displaceably arranged on the cylinder section 156, its internal diameter being adapted to the external diameter of the cylinder section 156 and its external diameter being adapted to the internal diameter of the guiding cylinder 56. A second pressure member 220 in the form of a helical spring is supported on the proximal side on the actuating member 218 and on the distal side on the side face 154. A diameter of the second pressure member 220 is somewhat larger than an external diameter of the valve disc 210.

A third pressure member 222 is supported on the proximal side also on the actuating member 218, but on the distal side on the valve disc 210. A spring constant of the second pressure member 220 is somewhat greater than a spring constant of the third pressure member 222. The second pressure member 220 presses the actuating member 218 against the stop surface 216.

The third pressure member 222 presses the valve disc 210 against the sealing elements 206 and 208 and thus closes the bore 200.

The actuating element 32 extends beyond the pivot axis 34 and defines a lever arm 224, which is fork-shaped and comprises two legs 226 extending parallel to each other. It is arranged such that the legs 226 of the fork-shaped lever arm 224 lie directly against the actuating member 218 on its side face 228 facing in the proximal direction. When the actuating element 32 is pivoted about the pivot axis 34 in the direction towards the gripping area 30, the legs 226 are moved in the distal direction, take the actuating member 218 along with them and displace it in the distal direction.

The way in which the instrument 10 operates, in particular, also the way in which the regulating device 66 operates, will be explained below with reference to the Figures.

In FIGS. 1 to 3a, the instrument 10 is shown in its basic position. The actuating element 32 is then unactuated. The source of pressurized gas 48 is in fluid connection with the inner space 178. The working pressure of the pressurized gas provided by the source of pressurized gas 48 acts on the annular flange 124 and presses it against the annular face 196. A valve 230, which is defined by the bore 194 together with the annular flange 124 and the sealing element 126, assumes, in the basic position of the instrument 10, a closed position. The pressurized gas is, therefore, unable to flow through the bore 194. The resetting member 76 presses the working piston 68 in the proximal direction. The piston disc 70 lies against the piston disc 86, which is moved up to the flange 58. The piston disc 112, which is fixedly connected to the piston disc 86, is, therefore, also forced to move in the proximal direction. The first pressure member 198 presses the piston disc 152 in the proximal direction also against the annular flange 124. The second pressure member 220 presses the actuating member 218 in the proximal direction against the stop surface 216, and the third pressure member 222 presses the valve disc 210 against the sealing elements 204 and 206 and closes the bore 200. The bore 200 together with the valve disc 210 and the sealing elements 206 and 208 defines a ventilation valve 232, which can only be opened against the action of the third pressure member 222. The valve 230 can only be opened against the action of the first pressure member 198.

Figure 4A:
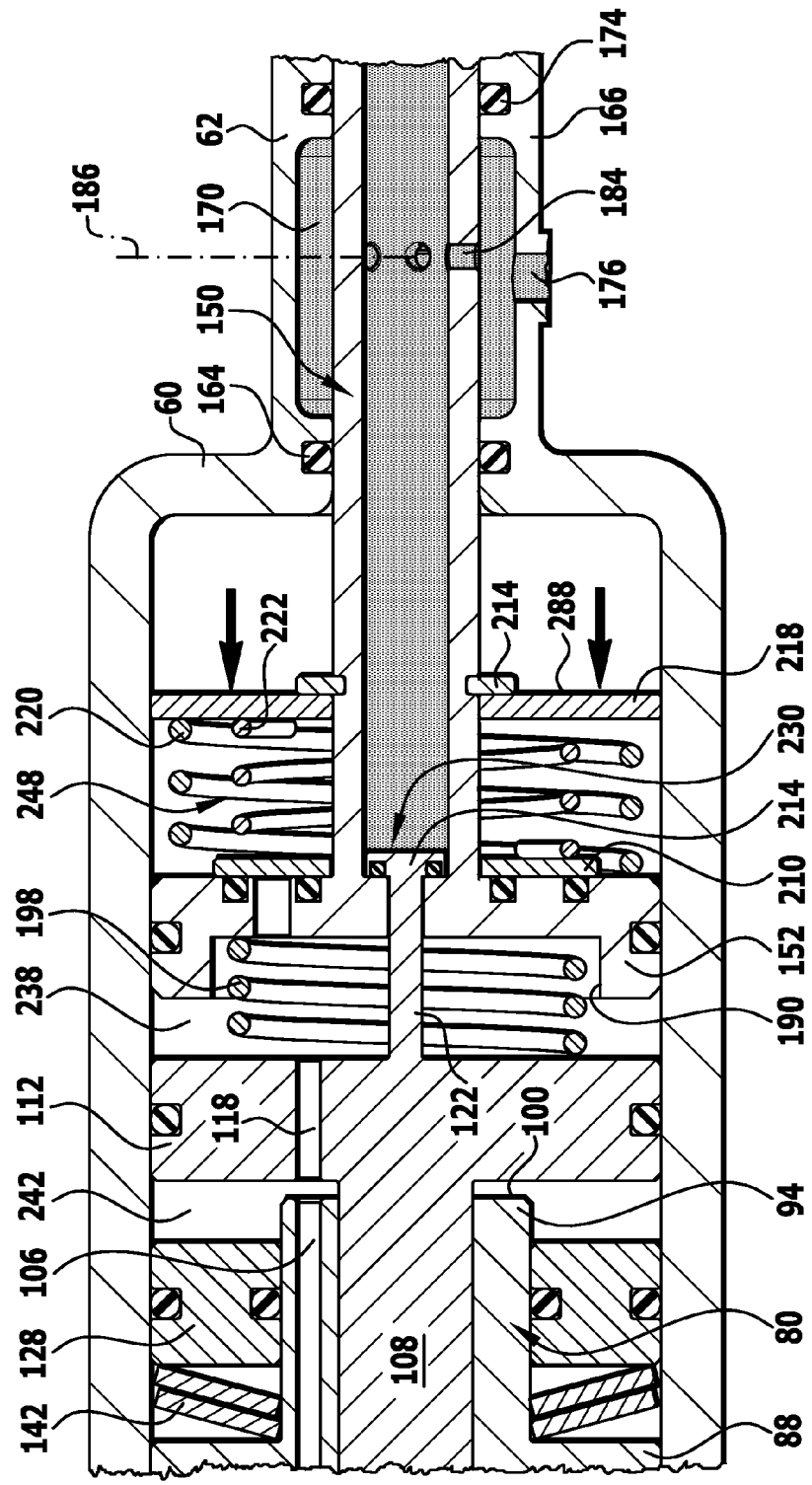
FIG. 4a shows an enlarged view of area D in FIG. 4.
Figure 5:
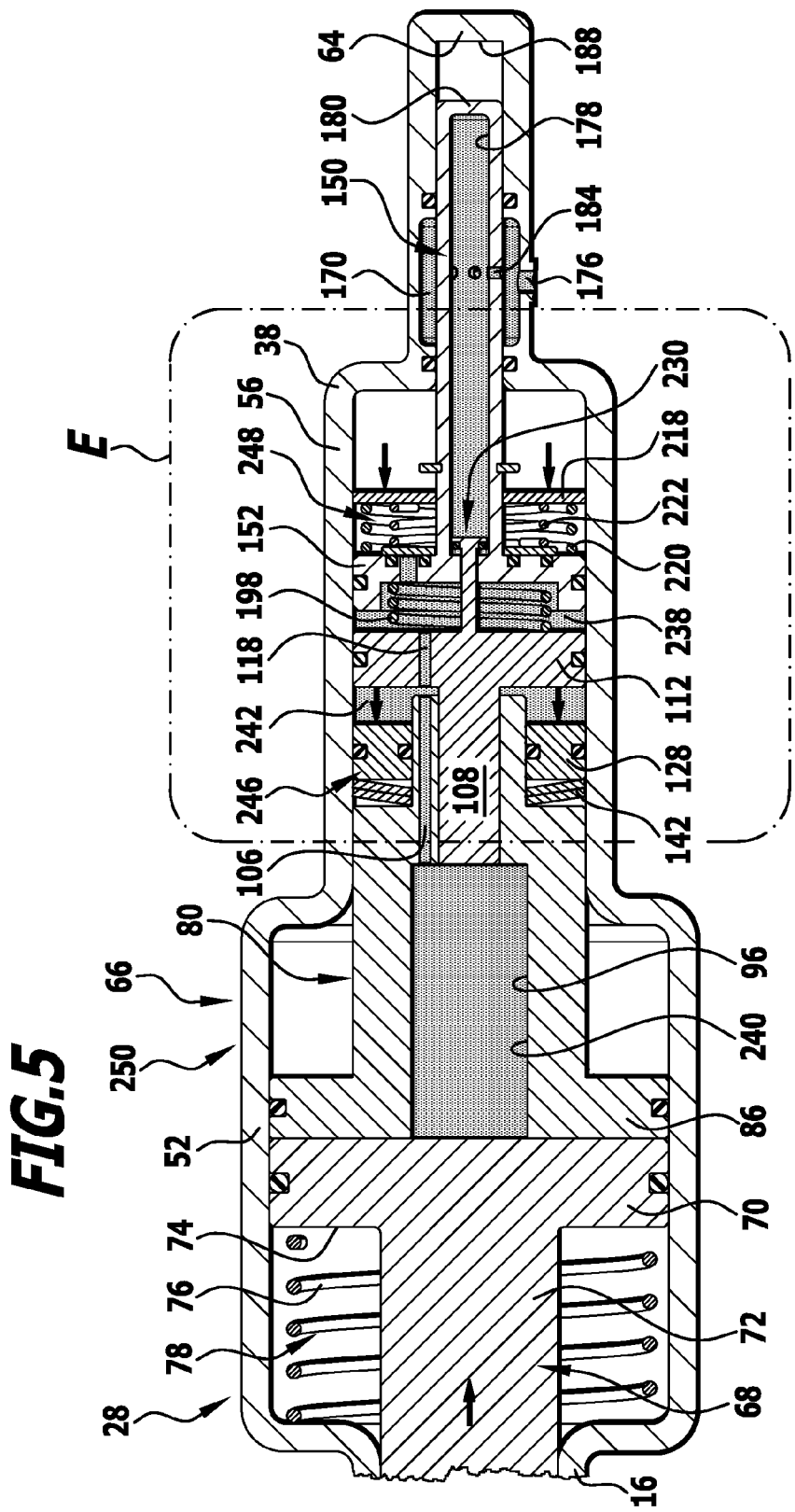
FIG. 5 shows a view in analogy with FIG. 3 still in the first work area of the instrument with the pressure of the pressurized gas increasing in the work space.
Figure 5A:
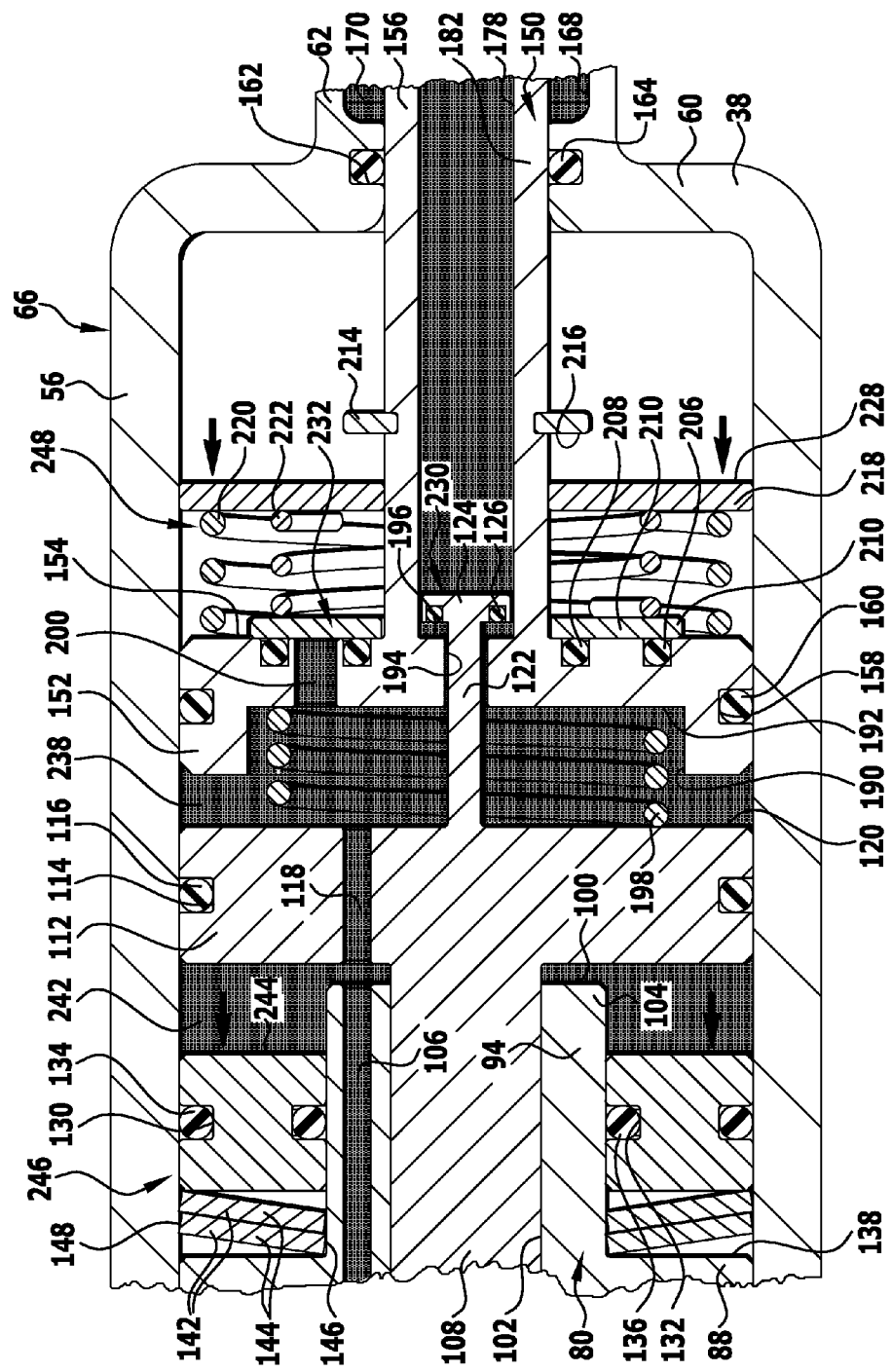
FIG. 5a shows an enlarged view of area E in FIG. 5.
Figure 7:
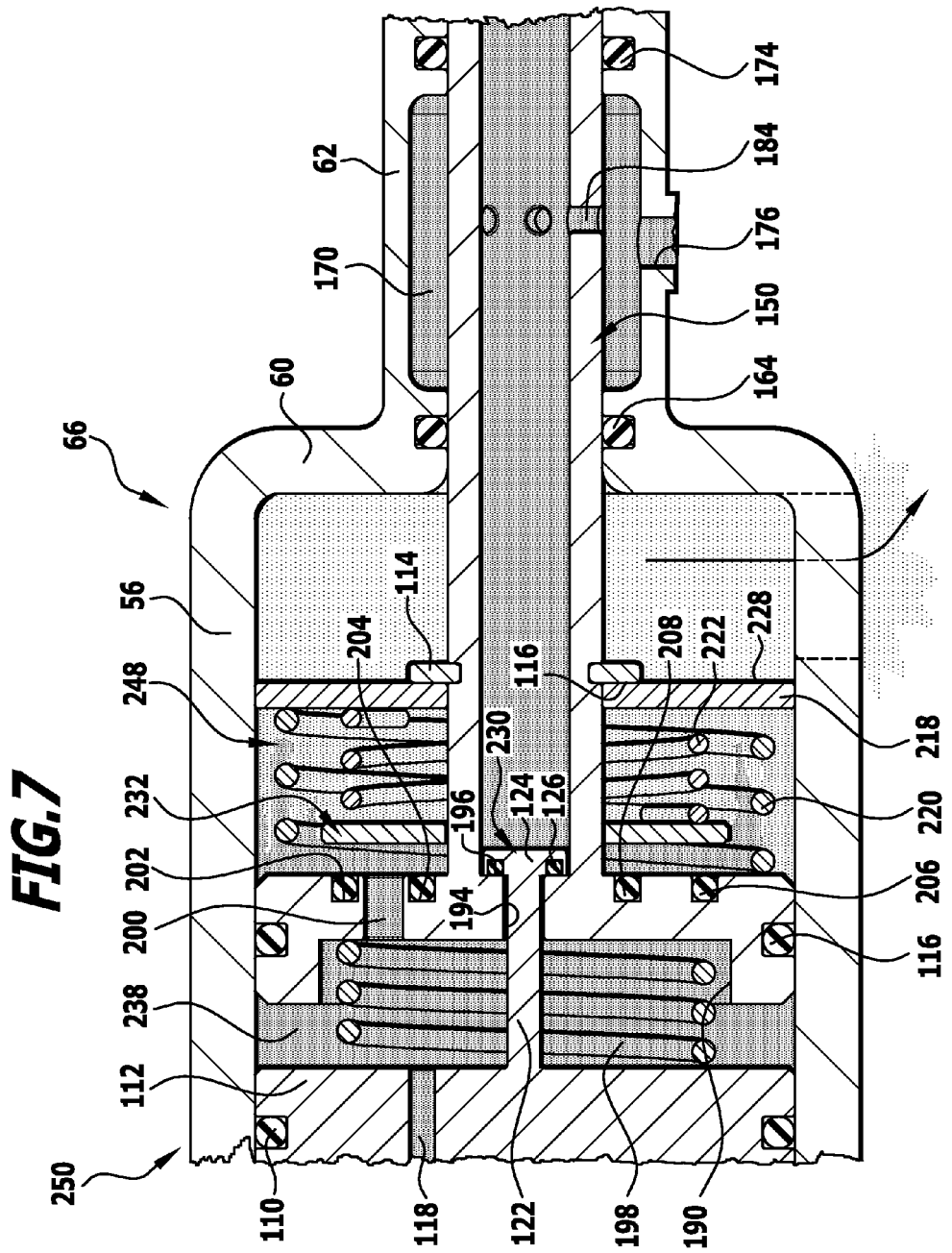
FIG. 7 shows an enlarged view of the regulating device of the instrument when ventilating the work space.

The force applied by the first pressure member 198 is slightly greater than the sum of the forces applied by the second and third pressure members 220, 222. If only low forces are counteracting the working piston 68 in the area of the cutting edge 26 defining tool elements 234 and 236 and in the area of the anvil part 20, then as a result of pivoting of the actuating element 32 in the direction towards the gripping area 30, the actuating member 218 is moved in the distal direction. In this first or mechanical work area of the instrument 10, movement of the working piston 68 occurs solely as a result of the feed force applied with the actuating element 32 in the distal direction. The actuating force introduced is transmitted via the second pressure member 220 and the third pressure member 222 onto the piston disc 152 and by means of the first pressure member 198 onto the piston disc 112. The working piston 68 supported directly on the piston disc 86 is thus moved in the distal direction without the assistance of pressurized gas. The first work area of the instrument 10 is shown in FIGS. 4 and 4a.

If the resistance between the tool elements 234 and 236 increases, and the force acting there exceeds the sum of the forces applied by the second pressure member 220 and by the third pressure member 222, then the pressure members 220 and 222 are compressed. The first pressure member 198 is also compressed, as a result of which the valve 230 opens, and pressurized gas can flow from the inner space 170 into the annular space 238 defined between the piston discs 112 and 152, in which the first pressure member 198 is arranged. The pressurized gas can continue to flow in until a balance of forces is established again between the sum of the force applied by the first pressure member 198 and the force prevailing due to the pressurized gas in the annular space 238 on the distal side of the piston disc 152 and the sum of the forces applied by the pressure members 220 and 222 on the other side of the piston disc 152. Pressurized gas is thus successively introduced into the annular space 238 by pivoting the actuating element 32 towards the gripping area 30. However, the working piston 68 still lies against the supporting element 80.

The annular space 238 is in fluid connection with a work space 240 defined by the blind hole 96 via the bores 118 and the bores 106. However, the prevailing gas pressure is also present in an annular space 242 between the clamping piston 128 and the piston disc 112 and acts on an annular face 244, facing in the proximal direction, of the clamping piston 128.

Above a certain gas pressure in the instrument 10, a locking device generally designated by reference numeral 246 is activated. It comprises the clamping piston 128 and the clamping elements 142. The piston disc 112 is then displaced in the direction towards the clamping piston 128, and with the assistance of the pressure prevailing in the pressurized gas, the clamping piston 128 is moved in the distal direction and presses the outer side 144, lying against it, of the disc 144 in the distal direction, as a result of which the supporting element 80 and the guiding cylinder 56 are clamped against each other. The working piston 68 is supported in the described manner on the supporting element 80 which is secured to the guiding cylinder 56 by the locking device 246 and is thus decoupled from movement of the actuating member 218. In addition, a clamping force acting between the supporting element 80 and the guiding cylinder 56 increases as the working pressure increases.

Upon further movement of the actuating element 32 in the direction towards the gripping area 30, the pressure members 220 and 222 are shortened further, so that the pressure prevailing in the work space 240 can rise up to a maximum. This prevailing pressure brings about the desired high force between the tool elements 234 and 236 by the pressurized gas in the work space 240 pressing the working piston 68 in the distal direction.

As described, the instrument 10 operates below a prescribed limit force, which can be set by appropriate choice of the pressure members 198, 220 and 222, in the first or mechanical work area. Only above the limit force is a second or pneumatic work area defined by the regulating device 66, in which the working piston 68 is moved in the distal direction only by being acted upon with pressurized gas. This second work area is shown in FIGS. 6 and 6a.

With the instrument 10, a desired maximum force can thus be applied solely by the pressurized gas. To reduce gas consumption to a minimum, in particular, when a pressurized gas container 42 is used, the pressurized gas is only activated additionally by the regulating device 66 when high forces are acting.

A pressure regulator 248 of the instrument is formed by the valve 230 and the three pressure members 198, 220 and 222 together with the piston disc 152. It ensures that a working pressure of the pressurized gas is proportional to a force applied by an operator to the actuating element 32. The force applied by the working piston 68 can thus be infinitely increased, with the user availing of as high a degree of tactility as possible. Since a defined path of both the actuating element 32 and the actuating member 218 is also covered in the second or pneumatic work area due to a shortening of the pressure members 220 and 222, the tactility is also improved for the user in the second work area.

When the actuating member 218 is moved forwards, the force applied by the third pressure member 222 is always slightly greater than the pressure force acting on the valve disc 210, so that the pressurized gas cannot escape, in particular, not from the work space 240.

If the force acting on the actuating element 32 is reduced by the user and it is pivoted away from the gripping area 30, the pressure members 220 and 222 are lengthened during the return stroke of the working piston 68, so that the force applied by the third pressure member 222 is no longer sufficient to close the bore 200. The pressure in the instrument 10 drops owing to the pressurized gas escaping via the ventilation valve 232 until the force of the third pressure member 222 is sufficient again to close the bore 200. In this way, the pressure in the work space 240 drops proportionally to the path covered by the actuating member 218 in the proximal direction, albeit with a certain revertive control hysteresis.

To protect the instrument 10 against overpressure, it is possible to additionally, i.e., optionally, provide a pressure relief valve, not shown in the Figures, in particular, in all the described preferred embodiments of a surgical instrument, which is in fluid connection with the inner space 178.

Figure 8B:
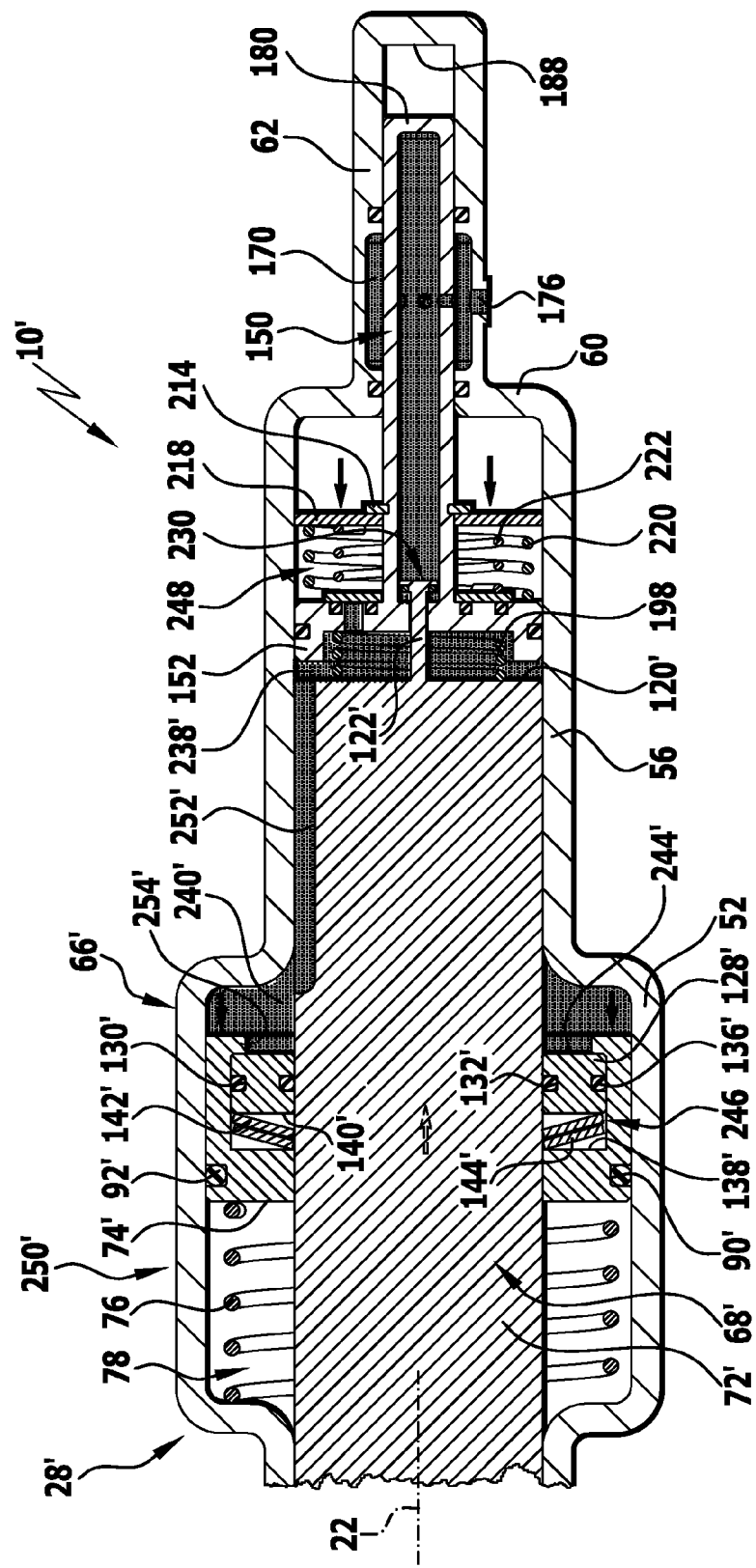
FIG. 8b shows a view corresponding to FIG. 8a with the working piston being moved solely by being acted upon by pressurized gas in the second work area.

An instrument, which is partly modified in relation to the surgical instrument 10, in the form of a bone punch, is represented diagrammatically in FIGS. 8a and 8b and designated in its entirety by reference numeral 10'. Essentially only those elements and parts of the instrument 10' and the way in which it operates, insofar as they differ from those of instrument 10, will be described below. It should also be noted that identical parts are designated by identical reference numerals, and in the case of parts which are similar or similar in their operation or parts corresponding to one another, the respective reference numeral is followed by a prime ("'").

The core piece of the instrument 10' is the drive part 28', which is somewhat modified in comparison with the drive part 28. The working cylinder 52, the guiding cylinder 56 and the bearing cylinder 62 form part of the housing 38 and a guiding device designated in its entirety by reference numeral 250'. They also serve to receive the drive of the instrument 10' and a regulating device designated in its entirety by reference numeral 66', which is somewhat modified in comparison with the regulating device 66.

A working piston 68' comprising a cylinder section 72' extending in the distal direction is held and guided in the working cylinder 52. The external diameter of the solid cylinder section 72' corresponds to the internal diameter of the shaft 16', which has the same internal diameter as the guiding cylinder 56. The cylinder section 72' may be formed integrally with the punch part 24. Optionally, the cylinder section 72' may also be detachable from the punch part 24 by means of a coupling device, not shown, in order to exchange the punch part 24 as required. A cylindrical valve pin 122', facing in the proximal direction, protrudes from a proximal end face 120' of the cylinder section 72' coaxially with the longitudinal axis 22. The valve pin 122' is identical in its construction and operation to the valve pin 122.

The cylinder section 72' has a longitudinal groove 252' extending parallel to the longitudinal axis 22. Starting from the end face 120', the longitudinal groove 252' extends in the distal direction and has a length which is somewhat smaller than an extent of the working cylinder 52 parallel to the longitudinal axis 22. In the instrument 10' this results, overall, in a construction in which the cylinder section 72' practically replaces the cylinder section 72 and the supporting element of the instrument 10.

The instrument 10' also comprises a locking device 246', which, however, is not formed in the area of the guiding cylinder 56, but so as to surround the cylinder section 72' in the area of the working cylinder 52. The locking device 246' comprises a supporting element 80' in the form of a piston comprising a piston disc 86'. This is provided with a bore 102' coaxially with the longitudinal axis 22. An external diameter of the piston disc 86' corresponds to an internal diameter of the working cylinder 52. A sealing element 92' in the form of an O-ring is inserted in an annular groove 90', formed on an outer face facing away from the longitudinal axis 22, of the piston disc 86' in order to seal the supporting element 80' and the working cylinder 52 relative to each other.

On the proximal side, a short, sleeve-shaped cylinder section 94', which is integrally formed with the piston disc 86', protrudes from the piston disc 86' and is aligned coaxially with the longitudinal axis 22. An external diameter of the cylinder section 94' corresponds to the external diameter of the piston disc 86' and defines together with an outer face, facing away from the longitudinal axis, of the piston disc 86' a common cylinder surface. A short annular flange 254' facing in the radial direction towards the longitudinal axis 22 and defining an annular stop surface 256' facing in the distal direction protrudes at a proximal end 100' of the cylinder section 94'. The supporting element 80' and the cylinder section 72', therefore, delimit an annular space 242' which is open in the proximal direction.

A substantially disc-shaped clamping piston 128' is guided on the cylinder section 72' parallel to the longitudinal axis 22. It comprises two annular grooves 130' and 132', which are open facing in the radial direction away from the longitudinal axis 22 and in the radial direction towards the longitudinal axis 22, respectively, on cylinder surfaces, formed coaxially with the longitudinal axis 22, of the clamping piston 128'. Sealing elements 134' and 136' in the form of O-rings are inserted in the annular grooves 130' and 132' in order to seal the clamping piston 128' and the working cylinder 52 and the clamping piston 128' and the cylinder section 72', respectively, relative to each other.

Two identical clamping elements 142' in the form of discs 144' are arranged between an annular face 138', facing in the proximal direction and delimiting the annular space 242' on the distal side, of the piston disc 86' and an annular face 140', facing in the distal direction, of the clamping piston 128'. It is, of course, also possible for more than two clamping elements to be provided. Furthermore, they do not have to be of identical construction. The discs 144' do not define a plane perpendicular to the longitudinal axis 22, but are inclined somewhat relative to the longitudinal axis 22. Inner edges 146' of the discs 144', which face in the radial direction towards the longitudinal axis 22, are thus arranged somewhat more distally than outer edges 148' of the discs 144', which face away from the longitudinal axis 22. Adjacent to the inner edge 146', the more distal disc 144' preferably lies against the annular face 138', and, adjacent to its outer edge 148', the proximal disc 144' against the annular face 140'. A spacing between the stop surface 256' and the annular face 138' is selected such that an annular face 244', facing in the proximal direction, of the clamping piston 128' lies against the stop surface 256'. The clamping elements 142' hold the clamping piston 128' under pretension in abutment against the annular flange 254'.

The helical spring forming a resetting member 76 is supported on an annular face 74', facing in the distal direction, of the piston disc 86'. On the distal side, the resetting member 76 is supported on the inside on the flange 54. The resetting member 76 is configured as a pressure member and forms part of the resetting device 78, which moves the working piston 68', if no actuating forces introduced or requested by a user are acting on it, into its basic position, namely in the proximal direction until it, if the resetting member 76 has a corresponding length, in the extreme case lies against the flange 58. If the resetting member 76 is only half as long as the working cylinder 52, the supporting element 80' does not reach the flange 58. This is represented diagrammatically in FIG. 8a. Preferably, however, the resetting member 76 does have a sufficient length, so that the supporting element 80', in the basic position, lies against the flange 58. The working piston 68' is, therefore, displaceably guided in the guiding cylinder 56 and in the shaft 16', and thus at least partly by the guiding device 250', parallel to the longitudinal axis 22 in the distal and proximal directions. Optionally, it is also possible for a further resetting member, not shown in FIGS. 8a and 8b, to be provided, which, on the one hand, is supported on the inside on the flange 54 and, on the other hand, directly on the working piston 68', for example, on an annular flange protruding in the radial direction from the working piston 68' and arranged or formed in the area between the flange 54 and the annular face 74'.

Apart from the differences described above, the regulating device 66' corresponds constructionally to the regulating device 66, so that reference can essentially be had to the above description in conjunction with the instrument 10.

The way in which the instrument 10' operates, in particular, also the way in which the regulating device 66' operates differently from the regulating device 66, will be explained below with reference to the Figures.

In a basic position of the instrument 10', the actuating element 32 is unactuated. The source of pressurized gas 48 is in fluid connection with the inner space 178. The working pressure of the pressurized gas provided by the source of pressurized gas 48 acts on the annular flange 124 and presses it against the annular face 196. In the basic position of the instrument 10', the valve 230 assumes a closed position. The pressurized gas is, therefore, unable to flow through the bore 194. The resetting member 76 presses the supporting element 80' in the proximal direction. A position of the supporting element 80' in the basic position is predetermined by a length of the resetting member 76 configured as a pressure spring, which defines a maximum spacing between the flange 54 and the piston disc 86'. As shown in FIG. 8a, the end 100' is spaced somewhat from the flange 58. However, the resetting member 76 is preferably of such length that the end 100' lies against the flange. The end 120' then assumes its most proximal position.

The first pressure member 198 presses the piston disc 152 in the proximal direction also against the annular flange 124. The second pressure member 220 presses the actuating member 218 in the proximal direction against the stop surface 216. The third pressure member 222 presses the valve disc 210 against the sealing elements 204 and 206 and closes the bore 200. The bore 200 together with the valve disc 210 and the sealing elements 206 and 208 defines a ventilation valve 232, which may only be opened against the action of the third pressure member 222. The valve 230 can only be opened against the action of the first pressure member 198.

The force applied by the first pressure member 198 is slightly greater than the sum of the forces applied by the second and third pressure members 220, 222. If only low forces are counteracting the working piston 68' in the area of the cutting edge 26 defining tool elements 234 and 236 and in the area of the anvil part 20, then as a result of pivoting of the actuating element 32 in the direction towards the gripping area 30 the actuating member 218 is moved in the distal direction. In this first or mechanical work area of the instrument 10', movement of the working piston 68' occurs solely as a result of the feed force applied by the actuating element 32 in the distal direction. The actuating force introduced is transmitted via the second pressure member 220 and the third pressure member 222 onto the piston disc 152 and by means of the first pressure member 198 onto the end face 120' of the working piston 68', which is thus moved in the distal direction without the assistance of pressurized gas. The working piston 68' is then displaced in the distal direction relative to the supporting element 80', which is held in the basic position by the resetting member. The first work area of the instrument 10' is shown in FIG. 8a.

If the resistance between the tool elements 234 and 236 increases, and the force acting there exceeds the sum of the forces applied by the second pressure member 220 and by the third pressure member 222, then the pressure members 220 and 222 are compressed. The first pressure member 198 is also compressed, as a result of which the valve 230 opens and pressurized gas can flow from the inner space 178 into the annular space 238' defined between the end face 120' and the piston disc 152, in which the first pressure member 198 is arranged. The pressurized gas can continue to flow in until a balance of forces is established again between the sum of the force applied by the first pressure member 198 and the force prevailing due to the pressurized gas in the annular space 238' on the distal side of the piston disc 152 and the sum of the forces applied by the pressure members 220 and 222 on the other side of the piston disc 152. Pressurized gas is thus successively introduced into the annular space 238' by pivoting the actuating element 32 towards the gripping area 30 and acts, in particular, directly on the end face 120' of the working piston 68'. The end 100' still lies against the flange 58.

The annular space 238' is in fluid connection via the longitudinal groove 252' with a work space 240' which surrounds the cylinder section 72' in annular shape. The work space 240' is delimited by the flange 58, the working cylinder 52, the end 100' and the annular face 244'. The prevailing gas pressure, therefore, acts on the annular face 244', facing in the proximal direction, of the clamping piston 128' and on the end 100'.

Above a certain gas pressure in the instrument 10', the locking device 246' is activated. The prevailing gas pressure acts on the end 100' and on the ring face 244' and moves the supporting element 80' against the action of the resetting member 76 in the distal direction. The prevailing gas pressure and the force applied by the resetting member 76 to the supporting element 80' counteract each other. Once the force acting due to the pressurized gas in the work space 240' on the end 100' corresponds to the resetting force applied by the increasingly compressed resetting member 76, the gas pressure prevailing in the work space 240' acts on the proximal side on the clamping piston 128'. The latter presses in the distal direction against the clamping elements 142'. The clamping piston 128' presses the outer side, lying against it, of the disc 144 in the distal direction, as a result of which the supporting element 80' and the cylinder section 72' are clamped against each other.

In the described manner, the working piston 68' forms a unit with the supporting element 80' secured by means of the locking device 246' to the cylinder section 72'. The gas pressure prevailing in the instrument 10', therefore, acts not only, as described, directly on the working piston 68' via the end face 120', but, in addition, also indirectly via the supporting element 80', with an effective area, defined substantially by the end face 120', of the working piston 68' being increased by a stepped effective area defined by the end 100' and the end face 244' and facing transversely to the longitudinal axis 22 in the proximal direction. The supporting element 80' sealed relative to the working cylinder 52, therefore, forms part of the working piston 68' above a certain gas pressure. Owing to the described increase in the effective area of the working piston 68', a feed force acting thereon is increased, more particularly, once the effect of the locking device 246' starts.

When the actuating element 32 is moved further in the direction towards the gripping area 30, the pressure members 220 and 222 are further shortened, so that the pressure prevailing in the work space 240' can increase to a maximum. This prevailing pressure brings about the desired high force between the tool elements 234 and 236 by the pressurized gas in the annular space 238' and in the work space 240' pressing the working piston 68' in the distal direction.

As described, the instrument 10' operates below a predetermined limit force, which can be set by appropriate choice of the pressure members 198, 220 and 222, in the first or mechanical work area. Only above the limit force is a second or pneumatic work area defined by the regulating device 66', in which the working piston 68' is moved in the distal direction with the additional assistance of pressurized gas. This second work area is shown diagrammatically in FIG. 8b. In the second work area, the supporting element 80' is, so to speak, activated additionally to the working piston 68'. In the instrument 10 the supporting element 80 is interposed and results in a more distinctive separation between mechanical and pressurized gas-operated work areas.

With the instrument 10', too, a desired maximum force can thus be applied essentially solely by the pressurized gas. To reduce gas consumption to a minimum, in particular, when a pressurized gas container 42 is used, the pressurized gas is only activated additionally by the regulating device 66' when high forces are acting.

The pressure regulator 248 ensures that a working pressure of the pressurized gas is proportional to a force applied by an operator to the actuating element 32. The force applied by the working piston 68' can thus be infinitely increased, with the user availing of as high a degree of tactility as possible. Since a defined path of both the actuating element 32 and the actuating member 218 is also covered in the second or pneumatic work area due to a shortening of the pressure members 220 and 222, the tactility is also improved for the user in the second work area.

When the actuating member 218 is moved forwards, the force applied by the third pressure member 222 is always slightly greater than the pressure force acting on the valve disc 210, so that the pressurized gas cannot escape, in particular, not from the work space 240'.

If the force acting on the actuating element 32 is reduced by the user and it is pivoted away from the gripping area 30, the pressure members 220 and 222 are lengthened during the return stroke of the working piston 68', so that the force applied by the third pressure member 222 is no longer sufficient to close the bore 200. The pressure in the instrument 10' drops owing to the pressurized gas escaping through the ventilation valve 232 until the force of the third pressure member 222 is sufficient again to close the bore 200. In this way, the pressure in the work space 240' drops proportionally to the path covered by the actuating member 218 in the proximal direction, albeit with a certain revertive control hysteresis.

To protect the instrument 10' against overpressure, it is possible to additionally provide a pressure relief valve, not shown in the Figures, which is in fluid connection with the inner space 178.

In the described instruments 10 and 10', over the major part of the path covered by the working piston 68 and 68', respectively, on which no or only a low force acts between the tool elements 234 and 236, the force can be applied mechanically by the user. Only on the final part of the path is the full working force applied by the action of pressurized gas. With standard jaw widths of bone punches of 20 mm and standard working paths of approximately 5 mm, i.e., only about a fourth of the possible entire path or stroke of the working piston 68, it is only on a quarter of the entire stroke of the working piston 68 in the instrument in accordance with the invention that displacement occurs pneumatically, on three quarters of the path it occurs purely mechanically. As a result, the gas consumption can be reduced to about a quarter. Therefore, with the same amount of gas about four times as many actuations of the instruments 10 and 10' in accordance with the invention are possible with maximum working force than with instruments without the regulating devices 66 and 66', respectively.

The variably adjustable pressure regulator 248 thus enables in both instrument 10 and instrument 10' infinite alteration of the working pressure during operation. This ensures a maximum of tactility. Furthermore, the gas consumption can be reduced to a minimum by the described combination of mechanical and pneumatic feed. As a result, significantly smaller pressurized gas containers 42 can be used in comparison with conventional instruments, and the volume defined by the housing 38 can thereby be significantly reduced in comparison with known instruments.

The invention claimed is:

1. Surgical instrument operated by pressurized gas, comprising:
   two tool elements, at least one of the two tool elements comprising a movable tool element,
   a pressurized gas connection for connecting the instrument to a source of pressurized gas,
   a working piston for moving the movable tool element and adapted to be acted upon by the pressurized gas,
   an actuating element for actuating the instrument, and
   a regulating device coupled to the actuating element and to the working piston for regulating a feed force of the working piston,
   wherein:
   the regulating device is configured such that for feed forces below a predetermined limit force it defines a first piston work area in which the working piston is movable in a distal direction solely owing to a first feed force that can be applied with the actuating element,
   above the limit force the regulating device defines a second piston work area in which the working piston is movable in the distal direction by being acted upon by pressurized gas, and
   the movable tool element is movable over a maximum displacement path as a result of movement of the working piston in the first piston work area as a result of the first feed force, provided the predetermined limit force is not exceeded.

2. Surgical instrument in accordance with claim 1, wherein the regulating device is configured such that in the second piston work area a second feed force acting on the working piston as a result of the working piston being acted upon by pressurized gas is proportional to the first feed force applied with the actuating element.

3. Surgical instrument in accordance with claim 1, wherein the regulating device comprises a work space adapted to be acted upon by the pressurized gas, the work space being at least partially open in a direction towards the working piston.

4. Surgical instrument in accordance with claim 1, further comprising a supporting element which interacts with the working piston in at least one of the first and second piston work areas.

5. Surgical instrument in accordance with claim 4, wherein the working piston is supported in the first piston work area on the supporting element.

6. Surgical instrument in accordance with claim 4, wherein the working piston is coupled in the second piston work area to the supporting element.

7. Surgical instrument in accordance with claim 5, wherein the working piston is supported in the first piston work area directly on the supporting element.

8. Surgical instrument in accordance with claim 5, wherein the supporting element is movable in the distal direction in the first piston work area solely owing to the first feed force applied with the actuating element.

9. Surgical instrument in accordance with claim 5, wherein the regulating device comprises a locking device for temporarily securing the supporting element in the second piston work area.

10. Surgical instrument in accordance with claim 9, wherein the locking device comprises at least one locking member for temporarily securing the supporting element to a guiding device or to the working piston.

11. Surgical instrument in accordance with claim 9, wherein the locking device comprises a piston element adapted to be acted upon by the pressurized gas, the piston element being movable in the distal direction by being acted upon by the pressurized gas and is pressable against the at least one locking member to clamp the at least one locking member relative to the supporting element and relative to a guiding device or relative to the working piston.

12. Surgical instrument in accordance with claim 1, wherein an actuating force introduced via the actuating element is transmittable to an actuating member mounted so as to be movable parallel to the working piston.

13. Surgical instrument in accordance with claim 1, wherein the regulating device comprises a pressure regulator for regulating a gas pressure acting on the working piston in dependence upon an actuating force introducible via the actuating element.

14. Surgical instrument in accordance with claim 13, wherein the pressure regulator is configured to regulate the gas pressure acting on the working piston in dependence upon the actuating force introduced via the actuating element on an actuating member mounted so as to be movable parallel to the working piston.

15. Surgical instrument in accordance with claim 13, wherein the pressure regulator comprises a first pressure member for defining an opening force required to open a valve closing the first piston work area.

16. Surgical instrument in accordance with claim 15, wherein:
   an actuating force introduced via the actuating element is transmittable to an actuating member mounted so as to be movable parallel to the working piston,
   the regulating device comprises a second pressure member for transmitting an actuating force from the actuating member to the pressure regulator.

17. Surgical instrument in accordance with claim 16, wherein the regulating device comprises a third pressure member for transmitting an actuating force from the actuating member to the pressure regulator.

18. Surgical instrument in accordance with claim 3, wherein the regulating device comprises a ventilation valve for ventilating a work space of the regulating device.

19. Surgical instrument in accordance with claim 18, wherein a pressure regulating piston element comprises the ventilation valve or a part of the ventilation valve.

20. Surgical instrument in accordance with claim 17, wherein the first, second and third pressure members are arranged such that a force applied by the first pressure member counteracts forces applied by the second and third pressure members.

21. Surgical instrument in accordance with claim 17, wherein the first, second and third pressure members are configured such that a force applied by the first pressure member in the first piston work area is always greater than a sum of forces applied by the second and third pressure members.

22. Surgical instrument in accordance with claim 1, further comprising a resetting device for transferring the instrument from a working position into which the working piston has been moved in the distal direction back into a basic position in which the working piston assumes a most proximal position.

23. Surgical instrument in accordance with claim 1, further comprising a housing, wherein at least one of the pressurized gas connection, the working piston, the actuating element, and the regulating device is arranged or formed on or in the housing.

24. Surgical instrument in accordance with claim 1, wherein:
- a source of the pressurized gas is a gas container filled with the pressurized gas, and
- the gas container is releasably connectable to the pressurized gas connection.

25. Surgical instrument in accordance with claim 1, wherein the instrument is configured in the form of a bone punch.

* * * * *